US012576224B2

(12) United States Patent
Frederiksen et al.

(10) Patent No.: US 12,576,224 B2
(45) Date of Patent: Mar. 17, 2026

(54) RESUSCITATOR

(71) Applicant: AMBU A/S, Ballerup (DK)

(72) Inventors: Birgitte Lidegaard Frederiksen, Virum (DK); Jakob Bønnelykke Kristensen, Ølstykke (DK); Alex Etwil, Albertslund (DK)

(73) Assignee: AMBU A/S, Ballerup (DK)

( * ) Notice: Subject to any disclaimer, the term of this patent is extended or adjusted under 35 U.S.C. 154(b) by 609 days.

(21) Appl. No.: 18/031,333

(22) PCT Filed: Oct. 4, 2021

(86) PCT No.: PCT/EP2021/077256
§ 371 (c)(1),
(2) Date: Apr. 11, 2023

(87) PCT Pub. No.: WO2022/078797
PCT Pub. Date: Apr. 21, 2022

(65) Prior Publication Data
US 2023/0372649 A1 Nov. 23, 2023

(30) Foreign Application Priority Data
Oct. 15, 2020 (DK) .......................... PA 2020 70693

(51) Int. Cl.
*A61M 16/00* (2006.01)
*A61M 16/08* (2006.01)
(Continued)

(52) U.S. Cl.
CPC .... *A61M 16/0084* (2014.02); *A61M 16/0078* (2013.01); *A61M 16/0816* (2013.01);
(Continued)

(58) Field of Classification Search
CPC .......... A61M 16/0078; A61M 16/0084; A61M 16/06; A61M 16/0816; A61M 16/1055;
(Continued)

(56) References Cited

U.S. PATENT DOCUMENTS 1,171,109 A 2/1916 Dust
3,196,866 A 7/1965 Adams
(Continued)

FOREIGN PATENT DOCUMENTS

CN 201542910 U 8/2010
CN 206979809 U 2/2018
(Continued)

OTHER PUBLICATIONS

First examination report of Denmark Patent Application No. PA 2020 70693, mailed Mar. 29, 2021, 9 pages.
(Continued)

*Primary Examiner* — Joseph D. Boecker
(74) *Attorney, Agent, or Firm* — Faegre Drinker Biddle & Reath LLP

(57) ABSTRACT

The resuscitator (1) includes a self-inflating squeeze bag (2) having an inlet opening accommodating an inlet valve arrangement (6) adapted to allow inflow of air into the squeeze bag and to prevent outflow of air from the squeeze bag through the inlet opening and an outlet opening accommodating a patient valve arrangement (8) adapted to allow outflow of air from the squeeze bag into the patient valve housing and adapted to prevent inflow of air into the squeeze bag through the outlet opening. The patient valve housing includes a patient connection port (9) for ventilation of a patient and a patient expiration outlet port (10) for outlet of exhaled gas from the patient valve housing to the surroundings. The resuscitator includes a filter arrangement (11) located upstream the outlet opening of the squeeze bag in
(Continued)

order to filter air before reaching the patient valve arrangement from the squeeze bag.

20 Claims, 15 Drawing Sheets

(51) Int. Cl.
    *A61M 16/10*         (2006.01)
    *A61M 16/20*         (2006.01)

(52) U.S. Cl.
    CPC ...... *A61M 16/1055* (2013.01); *A61M 16/107* (2014.02); *A61M 16/208* (2013.01); *A61M 2205/7509* (2013.01); *A61M 2205/7518* (2013.01)

(58) Field of Classification Search
    CPC .............. A61M 16/107; A61M 16/208; A61M 2205/7509; A61M 2205/7518
    See application file for complete search history.

(56) References Cited

U.S. PATENT DOCUMENTS

| | | | | | |
|---|---|---|---|---|---|
| 3,216,413 | A | * | 11/1965 | Arecheta Mota . | A61M 16/0009 128/205.13 |
| 3,342,177 | A | * | 9/1967 | Clementz .......... | A61M 16/0057 128/205.12 |
| 3,366,133 | A | | 1/1968 | Johannisson | |
| 3,548,822 | A | | 12/1970 | Seeler | |
| 4,239,038 | A | | 12/1980 | Holmes | |
| 4,299,215 | A | * | 11/1981 | Anon ................ | A61M 16/0093 128/200.24 |
| 4,782,831 | A | | 11/1988 | Gallant | |
| 4,821,712 | A | | 4/1989 | Gossett | |
| 4,870,962 | A | | 10/1989 | Sitnik | |
| 5,163,424 | A | | 11/1992 | Kohnke | |
| 5,222,491 | A | * | 6/1993 | Thomas .............. | A61M 16/107 417/478 |
| 5,372,130 | A | | 12/1994 | Stern et al. | |
| 5,383,786 | A | | 1/1995 | Kohnke | |
| 5,404,873 | A | | 4/1995 | Leagre et al. | |
| 5,427,091 | A | | 6/1995 | Phillips | |
| 5,628,305 | A | | 5/1997 | Melker | |
| 5,722,394 | A | | 3/1998 | Loescher | |
| 5,791,340 | A | | 8/1998 | Schleufe et al. | |
| 5,803,074 | A | | 9/1998 | Pope | |
| 6,578,574 | B1 | | 6/2003 | Køhnke | |
| 7,261,105 | B2 | | 8/2007 | Fukunaga et al. | |
| 2001/0029950 | A1 | | 10/2001 | Haubeil | |
| 2004/0007235 | A1 | | 1/2004 | Rafoss | |
| 2006/0191536 | A1 | | 8/2006 | Kroupa et al. | |
| 2007/0039619 | A1 | * | 2/2007 | Kohnke ........... | A61M 16/0057 128/205.24 |
| 2007/0169780 | A1 | * | 7/2007 | Halpern ........... | A61M 16/0057 128/205.15 |
| 2008/0314386 | A1 | | 12/2008 | Myklebust et al. | |
| 2012/0012111 | A1 | | 1/2012 | Howe, Jr. et al. | |
| 2023/0173215 | A1 | * | 6/2023 | Winkler ............. | B01D 46/0002 128/205.29 |

FOREIGN PATENT DOCUMENTS

| | | |
|---|---|---|
| CN | 211962760 U | 11/2020 |
| EP | 0818217 A1 | 1/1998 |
| WO | 2006091829 A2 | 8/2006 |

OTHER PUBLICATIONS

International Search Report and Written Opinion of International Application No. PCT/EP2021/077256, mailed Feb. 28, 2022.

* cited by examiner

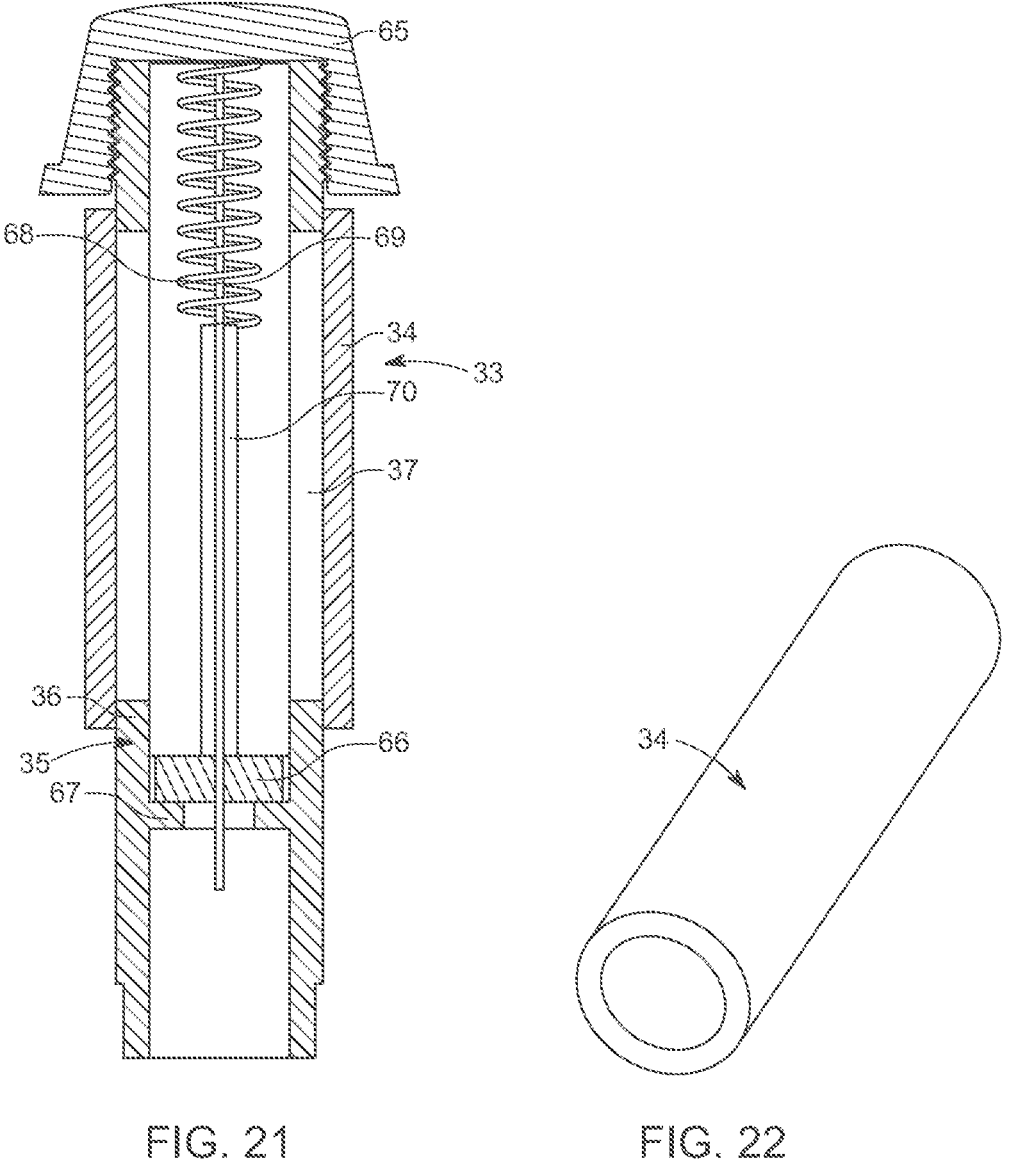
FIG. 21                    FIG. 22

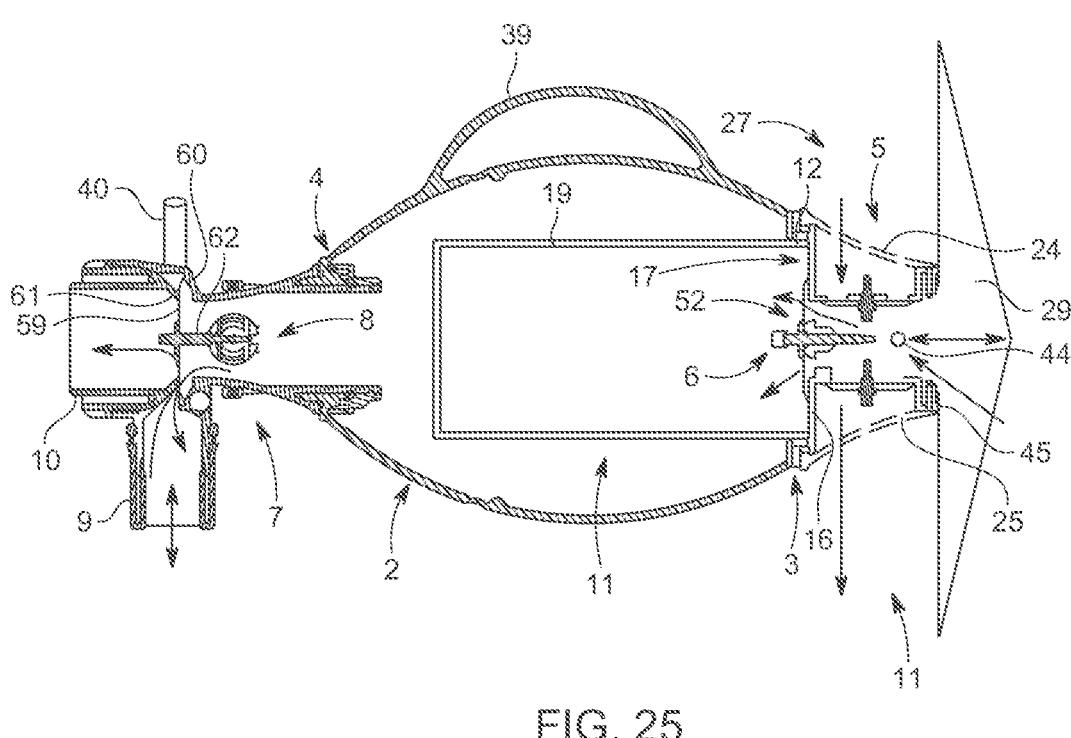
FIG. 25
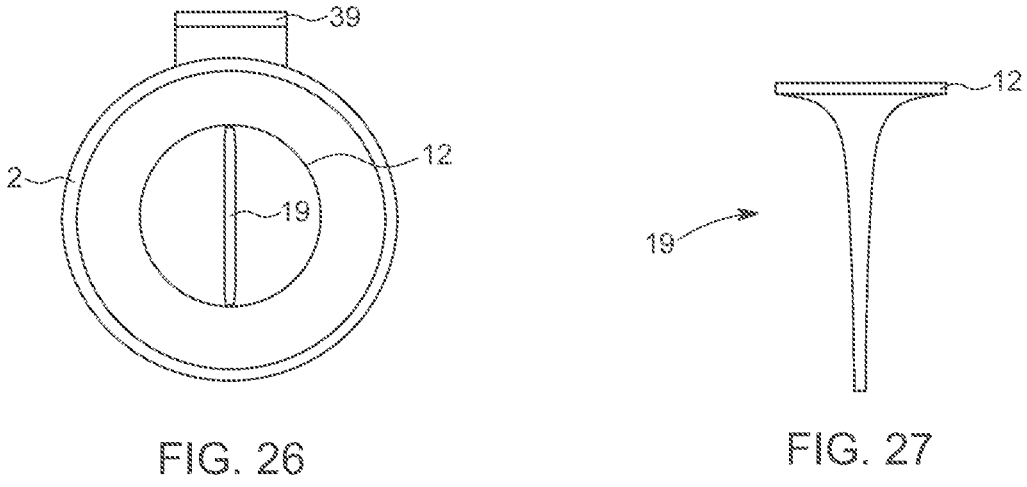
FIG. 26                    FIG. 27

RESUSCITATOR

CROSS-REFERENCE TO RELATED APPLICATIONS

This application is a National Phase entry under 35 U.S.C. § 371 of International Application No. PCT/EP2021/077256, filed Oct. 4, 2021, which claims the benefit of and priority from Denmark Patent Application No. PA 2020 70693, filed Oct. 15, 2020. The foregoing applications are incorporated by reference herein in their entirety.

TECHNICAL FIELD

The present disclosure relates to a resuscitator including a self-inflating squeeze bag. More particularly, the present disclosure relates to a resuscitator including a self-inflating squeeze bag and a filter arrangement.

BACKGROUND

U.S. Pat. No. 5,163,424 (Ambu International A/S) discloses a disposable resuscitator comprising an elastically compressible elongated squeeze bag having a first opening, a one-way valve for the intake of oxygen-containing gas into the bag mounted in said first opening, a second opening which is in airtight communication with a valve housing in the form of a transparent pipe having a pipe stub for the attachment of the resuscitator to a facial mask, and an outlet for exhalation air.

WO 2006/091829 A2 discloses a bag mask resuscitator including a flexible tubing having a proximal end and a distal end with the proximal end engaged to a resuscitation bag and the distal end adapted for engagement with a valve assembly. The valve assembly includes a coupling member adapted for quick engagement and disengagement of the flexible tubing from the valve assembly using a simple action.

U.S. Pat. No. 3,216,413 discloses a portable artificial respirator in the form of two bellows arranged one inside the other. The inner bellows form a volume for the intake of fresh air. The volume made up by the space between the inner bellows and the outer bellows is for the extraction of foul air. A drilled plate placed outside air intake valves may be provided with a breathing filter. The device has a T-tube that also acts as a handle so the operator can pump in an up down movement to alternately fill the inner volume with air by pulling the handle up and ventilate the air to the patient by pressing the handle down towards the patient's face. However, the device is not self-inflating and does not include an elastic squeeze bag.

EP 0 818 217 A1 discloses a closed circuit breathing bag for a person that breathes spontaneously and is not a resuscitator that assists in ventilating a patient. The exhaled CO2 is converted to O2 in the filter in a carbon filter that contains potassium superoxide. This allows the person to re-breath his/her own exhalation air as it is enriched with O2 when passing the carbon filter. Therefore, this is a completely different technology compared to a resuscitator which is being used for ventilating persons that are not breathing spontaneously.

CN 206979809 U, CN 201542910 U and US 2001/029950 A1 relate to resuscitator bags provided with an air filter at the air intake end.

Resuscitator bags are used for manual ventilation of patients in emergency care (pre-hospital) or in hospital care, e.g. by anaesthetists in the initial phase of anaesthesia for surgical procedures.

However, the aerosols contained in the surrounding air may contain particles and/or microbial or viral pathogens. Thus, there is a risk that particles and/or pathogens may be transferred to the patient resulting in a risk that the patient catches diseases of bacterial or viral origin (e.g. Covid-19 or other airways related diseases) if the inspiratory air contains such particles and/or pathogens.

Furthermore, the aerosols contained in the expiration air form the ventilated patient may contain microbial or viral pathogens that are spread to the environment surrounding the patient and thus also the operator and/or clinician (anaesthetist, nurse, pre-hospital emergency care etc.) providing the manual ventilation to the patient. Thus, there is a risk that pathogens may be transferred from the patient to the operator resulting in a risk that the operator catches diseases of bacterial or viral origin (e.g. Covid-19 or other airways related diseases) if the operator inhales aerosols expelled from the patient through the outlet on the PEEP valve on the resuscitator bag.

In some situations, a filter (catching aerosols including pathogen bacteria and/or virus present herein) is provided on the patient inspiratory port and thus between the face mask, laryngeal mask or ET tube and the resuscitator bag while performing manual ventilation of the patient. This filter does, however, increase the dead space of the ventilatory pathway leading to increased rebreathing of air, which may result in hypercapnia. The dead space is that volume of previously exhaled gas which is delivered to the patient in the succeeding inflation. Also, placing the filter at the patient inspiratory port will lead to an increased inspiratory and expiratory resistance.

US 2012/0012111 A1 discloses an application for a Positive End-Expiratory Pressure (PEEP) valve including a filter media in the air flow between a patient interface and exit vent(s). The patient interface is connected to a patient airway system and the exit vents exhaust exhalation gasses into the atmosphere. The filter prevents or reduces the passage of microbes from the patient's exhalation gasses into the atmosphere. The PEEP valve provides positive gas pressure to a patient's lungs, requiring a predetermined exhalation gas pressure to be exceeded before releasing exhalation gasses into the atmosphere. However, the filter media is arranged in a filter holder inserted between the patient airway system and the PEEP valve, thereby increasing the size of the entire resuscitator arrangement.

SUMMARY

An object of the present disclosure is to provide a resuscitator provided with a filter arrangement for the inspiratory air of the patient without increasing the dead space of the ventilatory pathway and without any substantial increase of the inspiratory and/or expiratory resistance.

In view of this object, the resuscitator includes a filter arrangement located upstream the squeeze bag outlet opening in order to filter air before reaching the patient valve arrangement from the squeeze bag.

In this way, by filtering the inspiratory air of the patient before the air reaches the patient valve arrangement from the squeeze bag, the dead space associated with the patient connection port and its connection with the patient airway device (e.g. face mask, supraglottic airway device, tracheal tube etc.) is not influenced by the filter arrangement. Likewise, the expiratory resistance experienced by the patient is not influenced, and the inspiratory resistance may be influenced very little, depending on the size and location of the filter arrangement. Furthermore, when the squeeze bag is compressed, the inflation resistance may be influenced very little or not at all, also depending on the size and location of the filter arrangement.

In an embodiment, the filter arrangement is located inside the squeeze bag. Thereby, the overall dimensions of the resuscitator may be unaffected by the filter arrangement, and the resuscitator will be less bulky when the filter is arranged inside the squeeze bag. Furthermore, the filter area can be made larger when arranging the filter inside the squeeze bag. This allows for maximizing the filter area which may reduce inspiratory resistance.

In an embodiment, a peripheral edge of the filter arrangement fits a cross-section of a wall of the squeeze bag, and the peripheral edge of the filter arrangement is attached to the wall of the squeeze bag.

In an embodiment, the filter arrangement is attached at the squeeze bag outlet opening.

In an embodiment, the peripheral edge of the filter arrangement has been attached to the wall of the squeeze bag by assembling the squeeze bag from two complementary squeeze bag parts and sandwiching the peripheral edge of the filter arrangement between opposed edges of the complementary squeeze bag parts. Thereby, a strong connection between the peripheral edge of the filter arrangement and the wall of the squeeze bag may be obtained.

In an embodiment, the squeeze bag is elongated in a longitudinal direction extending from the squeeze bag inlet opening to the squeeze bag outlet opening, and the filter arrangement has a longitudinal direction being arranged obliquely to the longitudinal direction of the squeeze bag. Thereby, the filter area of the filter arrangement may be maximized. In particular, the filter area of a single sheet filter may be maximized.

In an embodiment, the filter arrangement is attached at the squeeze bag inlet opening. Thereby, when the squeeze bag is compressed, the inflation resistance may be influenced very little or not at all, depending on how much or whether the filter arrangement itself is deformed when squeezing the squeeze bag. If the filter arrangement itself is not deformed when squeezing the squeeze bag, the inflation resistance may not at all be influenced by the filter arrangement.

In a structurally particularly advantageous embodiment, the filter arrangement is attached to the squeeze bag inlet valve housing.

In an embodiment, the filter arrangement has a peripheral edge attached along a corresponding edge of a filter opening of the squeeze bag inlet valve housing.

In an embodiment, the filter arrangement has the form of a flat filter.

In an embodiment, the filter arrangement includes one or more pocket filters and/or filter bags. Thereby, the effective filtration area may be increased.

In an embodiment, the filter arrangement has the form of a filter bag having a ring-formed peripheral part extending away from the squeeze bag inlet opening and being arranged adjacent an inside wall of the bag. Thereby, the influence on the filter arrangement and consequently on the inflation resistance from squeezing the squeeze bag may be minimized, because the ring-formed peripheral part extending away from the squeeze bag inlet opening may flex towards the inner of the squeeze bag when the squeeze bag is squeezed. Therefore, squeezing the squeeze bag will not result in much air being pressed through the filter bag. Furthermore, the form of the filter bag having a ring-formed peripheral part extending away from the squeeze bag inlet opening may allow packing the resuscitator for transport by pressing opposed ends of the squeeze bag, corresponding to the ends provided with the squeeze bag inlet opening and the squeeze bag outlet opening, respectively, into the interior of the squeeze bag.

In an embodiment, the filter arrangement has the form of a pocket filter or filter bag being tapered in a direction extending away from the squeeze bag inlet opening. Thereby, the influence on the filter arrangement and consequently on the inflation resistance from squeezing the squeeze bag may be minimized, because the volume of air inside the pocket filter or filter bag may be less at a central area of the squeeze bag where the squeeze bag is squeezed.

In an embodiment, the filter arrangement has the form of a number of filter bags arranged in a ring-form adjacent an inside wall of the squeeze bag. Thereby, the influence on the filter arrangement and consequently on the inflation resistance from squeezing the squeeze bag may be minimized, because the number of filter bags arranged in a ring-form may flex towards the inner of the squeeze bag when the squeeze bag is squeezed. Therefore, squeezing the squeeze bag will not result in much air being pressed through the filter bags. Furthermore, the number of filter bags arranged in a ring-form may allow packing the resuscitator for transport by pressing opposed ends of the squeeze bag, corresponding to the ends provided with the squeeze bag inlet opening and the squeeze bag outlet opening, respectively, into the interior of the squeeze bag.

In an embodiment, the one or more pocket filters and/or filter bags is/are adapted to be maintained in shape by means of a flexible skeleton. Thereby, it may be ensured that the one or more pocket filters and/or filter bags are maintained in their optimal shape for filtering when the squeeze bag flexes elastically back to its normal form after it has been squeezed.

In an embodiment, the filter arrangement is located outside the squeeze bag. Thereby, the size of the filter arrangement is not limited by the squeeze bag. Furthermore, thereby the filter arrangement does not necessarily need to be flexible, because compression of the squeeze bag does not necessarily influence the filter arrangement.

In a structurally advantageous embodiment, the squeeze bag inlet valve housing has a peripheral inlet valve housing wall which extends beyond the squeeze bag inlet opening and is provided with a number of ambient air inlet openings for the intake of air from the surroundings into the squeeze bag inlet valve housing, and the filter arrangement is arranged to filter air flowing through the ambient air inlet openings.

In an embodiment, the peripheral inlet valve housing wall is cylindrical.

In an embodiment, the peripheral inlet valve housing wall is tapering in a direction away from the squeeze bag.

In an embodiment, the filter arrangement has the form of a filter material covering an inside of the peripheral inlet valve housing wall. Thereby, the filter material may be protected by means of the peripheral inlet valve housing wall.

In an embodiment, the filter arrangement has the form of a filter material covering an outside of the peripheral inlet valve housing wall. Thereby, the filter material may be easily accessible and may arranged as an optional fitting.

In an embodiment, the filter arrangement has the form of a ring-formed filter bag arranged on an outside of the peripheral inlet valve housing wall.

In an embodiment, the ring-formed filter bag extends beyond the inlet valve housing in a direction away from the squeeze bag.

In an embodiment, at least a part of the ring-formed filter bag surrounds an oxygen reservoir bag arranged at an end of the inlet valve housing opposed to the squeeze bag. Thereby, because the ring-formed filter may be arranged around the oxygen reservoir bag, the influence of the filter on the overall dimensions of the resuscitator may be minimized.

In an embodiment, the squeeze bag inlet valve housing has an inlet valve housing end wall facing away from the squeeze bag, the inlet valve housing end wall is provided with an ambient air inlet valve, and the filter arrangement has the form of a tubular filter extending from the ambient air inlet valve.

In an embodiment, the tubular filter extends in a direction away from the squeeze bag.

In an embodiment, the tubular filter extends in a transverse direction to the inlet valve housing.

In an embodiment, the filter arrangement includes a filter material having an effective filtration area which is greater than, preferably at least 25 times, more preferred at least 40 times, and even more preferred at least 50 times a minimum cross-sectional flow area of the patient connection port. Thereby, even if the filter arrangement is located inside the squeeze bag, when the squeeze bag is compressed, the inflation resistance may be influenced very little or not at all.

In an embodiment, the filter arrangement includes a filter material based on textiles. The filter material may generally form a bacterial and/or viral filter.

In an embodiment, the patient expiration outlet port is provided with a PEEP valve for the control of the flow and/or pressure at the patient expiration outlet port, and the PEEP valve has a PEEP valve filter. This may reduce and/or eliminate that the operator is exposed to pathogens (bacteria and/or virus) while manually ventilating a contagious patient using the resuscitator. Additionally, the risk of spreading of pathogens to the surroundings (e.g. in airborne aerosols) may be reduced and/or eliminated.

In an embodiment, the PEEP valve includes a PEEP valve housing having a peripheral PEEP valve housing wall, the peripheral PEEP valve housing wall is provided with a number of patient expiration outlet openings for outlet of exhaled gas from the PEEP valve housing to the surroundings, and the PEEP valve filter is arranged to filter air flowing through the patient expiration outlet openings.

In an embodiment, the peripheral PEEP valve housing wall is cylindrical.

In an embodiment, the peripheral PEEP valve housing wall is tapering in a direction away from the squeeze bag.

In an embodiment, the PEEP valve filter is covering an outside of the peripheral PEEP valve housing wall.

In an embodiment, the PEEP valve filter is integrated in the PEEP valve.

In an embodiment, the PEEP valve filter is adapted to click on the PEEP valve.

The present disclosure furthermore relates to a PEEP valve as described above for attachment to a patient expiration outlet port of a resuscitator of any suitable type. The PEEP valve is adapted for the control of the flow and/or pressure at the patient expiration outlet port, and the PEEP valve has a PEEP valve filter.

BRIEF DESCRIPTION OF THE FIGURES

The disclosure will now be explained in more detail below by means of examples of embodiments with reference to the very schematic drawing, in which

FIG. 21 is an axial section of another embodiment of a PEEP valve with a PEEP valve filter, for use with a resuscitator;

FIG. 22 is a perspective view of the PEEP valve filter of the PEEP valve of FIG. 19;

FIGS. 23 to 25 illustrate, seen in an axial section, further different embodiments of a resuscitator with a filter arrangement according to the present disclosure;

FIG. 26 is a cross-sectional view of the resuscitator of FIG. 25; and

FIG. 27 is a side view of a filter of the resuscitator of FIG. 25.

DETAILED DESCRIPTION

Figure 1:
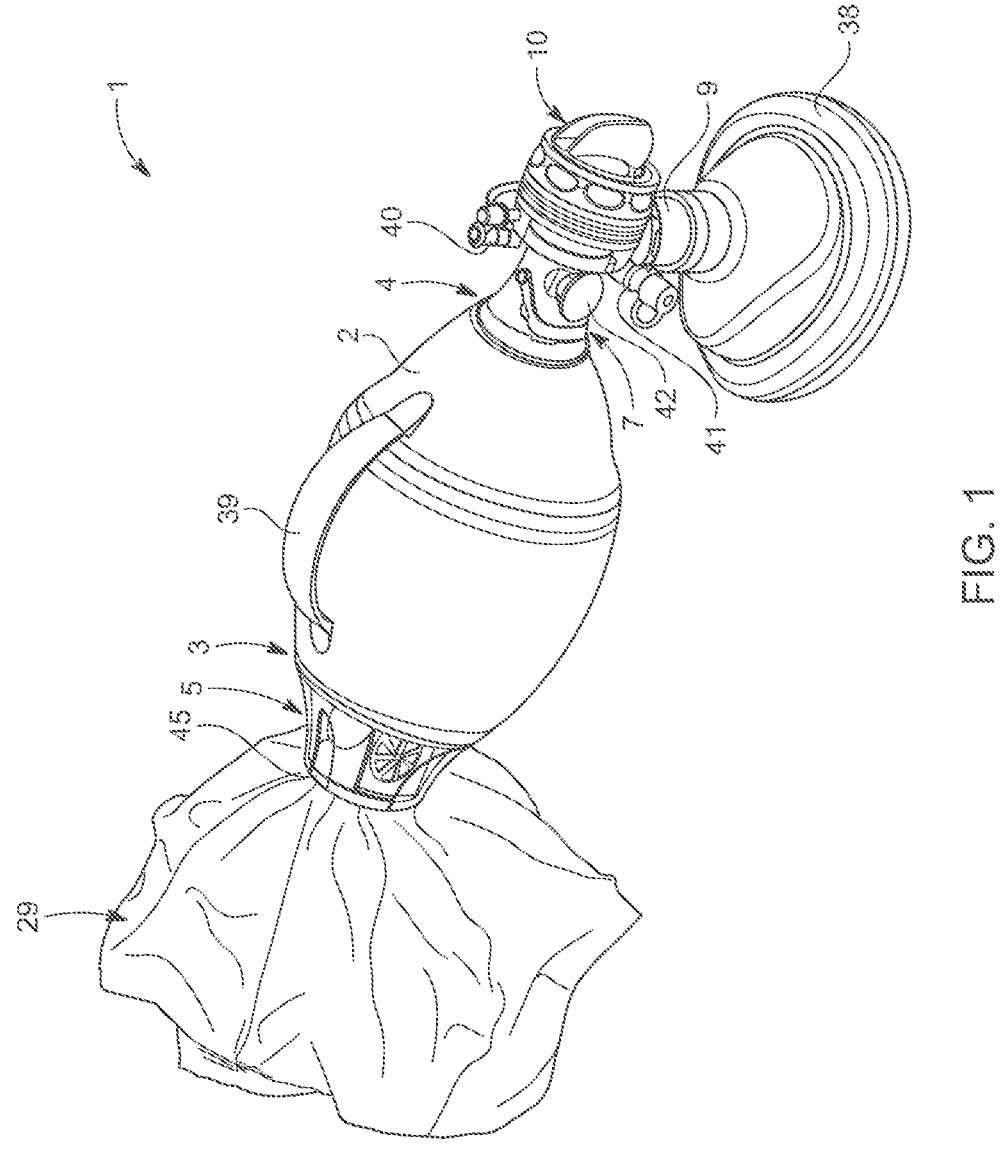
FIG. 1 is a perspective view of a prior art resuscitator including a self-inflating squeeze bag.

In the following, generally, similar elements of different embodiments have been designated by the same reference numerals.

FIG. 1 shows a well-known prior art resuscitator 1 including a self-inflating elastic squeeze bag 2, without filtration of the inspiratory air. The resuscitator 1 may in a manner well-known in the art be used for manual ventilation of patients in emergency care (pre-hospital) or in hospital care, e.g. by anaesthetists in connection with anaesthesia during surgical procedures. The self-inflating elastic squeeze bag 2 may for instance be made of styrene-ethylene-butylene-styrene block copolymer (SEBS) or poly vinyl chloride (PVC). The self-inflating function of the squeeze bag 2 is obtained in that the material of the squeeze bag 2 is an elastic material. Therefore, the squeeze bag 2 may be compressed by an operator from it relaxed state as illustrated in the figures to a compressed (not shown) state. Subsequently to being compressed by the operator, the compressed squeeze bag 2, when let free from its compression by the operator, will by means of its elasticity return to its relaxed state and thereby drag respiration air into the squeeze bag.

As seen in FIG. 1, the self-inflating squeeze bag 2 has a squeeze bag inlet opening 3 and a squeeze bag outlet opening 4. The squeeze bag inlet opening 3 accommodates a squeeze bag inlet valve housing 5 including a squeeze bag inlet valve arrangement 6 (not visible in FIG. 1) being adapted to allow inflow of air into the squeeze bag 2 and being adapted to prevent outflow of air from the squeeze bag 2 through the squeeze bag inlet opening 3. The squeeze bag outlet opening 4 accommodates a patient valve housing 7 including a patient valve arrangement 8 (not visible in FIG. 1) being adapted to allow outflow of air from the squeeze bag 2 into the patient valve housing 7 and being adapted to prevent inflow of air into the squeeze bag 2 through the squeeze bag outlet opening 4. The patient valve housing 7 further includes a patient connection port 9 for directing air to and from the patient airways and a patient expiration outlet port 10 for outlet of exhaled gas from the patient valve housing 7 to the surroundings. As seen in FIG. 1, the patient connection port 9 is provided with a face mask 38 for ventilation of a patient, but, alternatively, among others, the patient connection port 9 could be provided with a laryngeal mask or an endotracheal tube (ET tube) for ventilation of a patient.

As further seen in FIG. 1, the patient valve housing 7 is provided with a manometer port 40 with cap, a so-called M-port 41 for installation of medication or measurement of $CO_2$ and a pressure limiting valve 42, and the patient expiration outlet port 10 is provided with splash guards 39 in order to prevent an operator from splashes of fluid. Optionally, the patient expiration outlet port 10 may be provided with a PEEP valve 33 as illustrated in FIGS. 19 to 22 in order to control the pressure in a patient's lungs at the end of expiration. The squeeze bag inlet valve housing 5 is further provided with an oxygen reservoir bag 29 and an oxygen inlet connector 43 (not visible in FIG. 1) adapted to fill the oxygen reservoir bag 29 with oxygen from an oxygen supply. The squeeze bag 2 is provided with a support strap 39.

Figure 23:
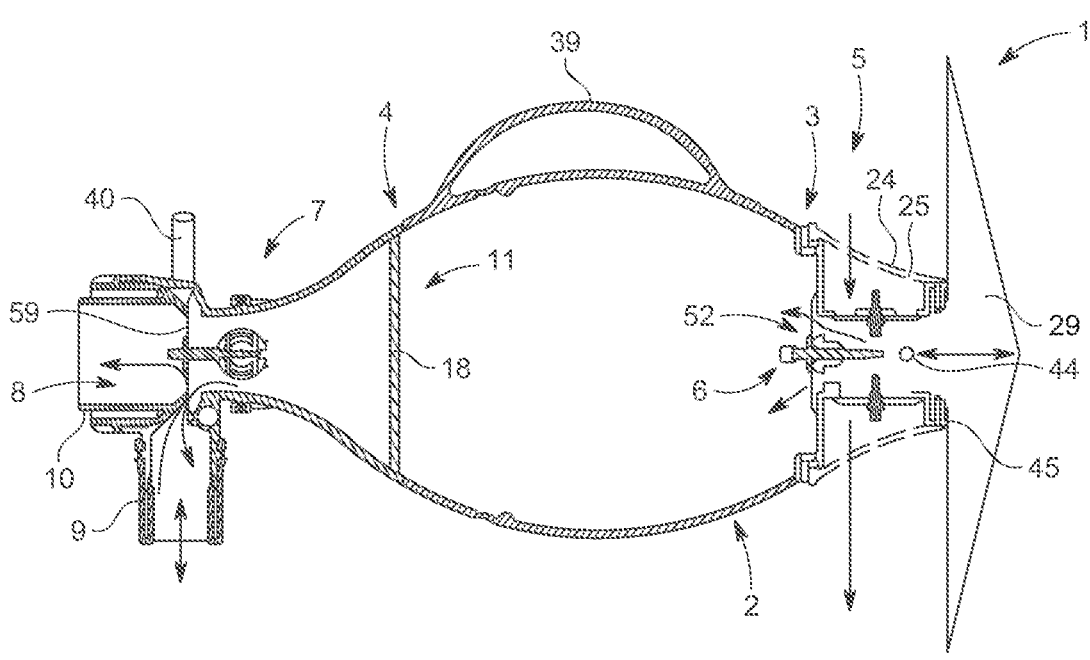

FIGS. 2 to 9 and 23 to 25 illustrate different embodiments of a resuscitator 1 of the same type as illustrated in FIG. 1, however, according to the present disclosure, provided with a filter arrangement 11 located upstream the squeeze bag outlet opening 4 in order to filter air before reaching the patient valve arrangement 8 from the squeeze bag 2. FIGS. 10 to 18 illustrate different embodiments of a resuscitator 1 of a somewhat different type than that of FIG. 1, however, according to the present disclosure, also provided with a filter arrangement 11 located upstream the squeeze bag outlet opening 4. In the different embodiments illustrated in FIGS. 2 to 18 and 23 to 25, the filter arrangement 11 is located inside the squeeze bag 2, at the squeeze bag inlet opening 3 or outside the squeeze bag 2. However, it is understood that according to the present disclosure, the filter arrangement 11 may also be located at the squeeze bag outlet opening 4, in arrangements corresponding to those illustrated at the squeeze bag inlet opening 3, and the filter arrangement 11 may further be located at the squeeze bag outlet opening 4 inside or outside the squeeze bag 2. FIG. 23 illustrates an embodiment in which the filter arrangement 11 is located inside the squeeze bag 2 at the squeeze bag outlet opening 4 in that the filter arrangement 11, in the form of a flat filter 18, is attached to the squeeze bag patient valve housing 7. The resuscitator 1 illustrated in FIG. 23 is of the same type as the resuscitator illustrated in FIG. 1, however, the patient valve housing 7 has been adapted somewhat in order to provide for a larger diameter of the patient valve housing 7 at the connection to the squeeze bag outlet opening 4. Thereby, the illustrated flat filter 18 may have a larger diameter. It is noted that the illustrated flat filter 18 in both the embodiment illustrated in FIG. 23 and the embodiment illustrated in FIG. 10 could be covered on one or both its sides by means of a respective possibly detachable grid, grille, perforated plate or other arrangement suitable to maintain the shape of the flat filter 18 and suitable to hold the flat filter 18 in place.

It is noted that in the embodiment illustrated in FIG. 23, the patient valve housing 7 may be connected detachably to the squeeze bag 2 so that the filter arrangement 11 may easily be replaced, if the need should arise, for instance because of a polluted filter. In fact, in all embodiments in which the filter arrangement 11 is located inside the squeeze bag 2, it could be advantageous if the patient valve housing 7 and/or the squeeze bag inlet valve housing 5 would be connected detachably to the squeeze bag 2 so that the filter arrangement 11 could easily be replaced. Likewise, filter arrangements 11 having constructions as shown in any of the FIGS. 2, 8, 10, 12 to 15 or 24 to 25 and being attached to the inlet valve housing 5, could alternatively be arranged at the squeeze bag outlet opening 4 as an alternative to the flat filter shown in FIG. 23.

FIGS. 2 to 9 and 23 to 25 additionally show the inlet valve arrangement 6 and the patient valve arrangement 8. In the embodiments illustrated in FIGS. 10 to 18, the inlet valve arrangement 6 is of a different type than that illustrated in FIGS. 2 to 9 and 23 to 25, whereas the patient valve arrangement 8 is of the same type as that illustrated in FIGS. 2 to 9 as well as 24 and 25. The oxygen inlet connector 43 is not visible in FIG. 1, but may be seen in FIGS. 10, 11, 12, 14 and 16. Furthermore, an oxygen inlet port 44 arranged in the squeeze bag inlet valve housing 5 and connected to the oxygen inlet connector 43 is visible in FIGS. 2 to 9. In all illustrated embodiments, the squeeze bag inlet valve housing 5 is provided with an oxygen reservoir bag connector port 45 to which the oxygen reservoir bag 29 is connected. As it is understood from the figures, the oxygen reservoir bag 29 may be filled with oxygen directly from the oxygen inlet connector 43 without any intermediate valves.

In the embodiments illustrated in FIGS. 2 to 9 and 23 to 25, the inlet valve arrangement 6 is arranged in the squeeze bag inlet valve housing 5 as follows.

Figure 2:
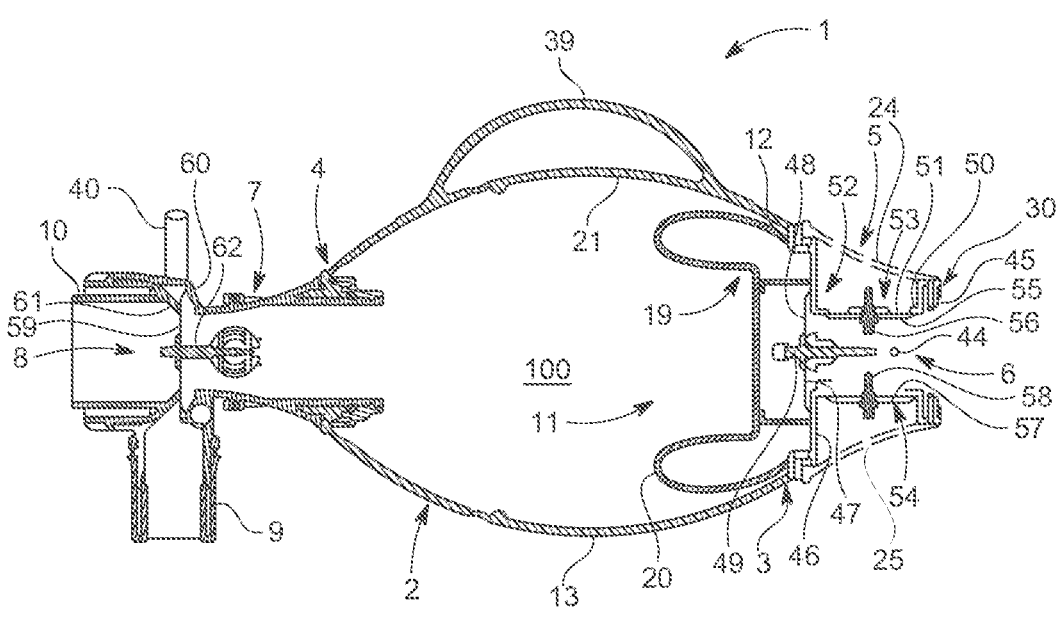
FIGS. 2 to 10 illustrate, seen in an axial section, different embodiments of a resuscitator with a filter arrangement according to the present disclosure.

Referring to FIG. 2, a resuscitator 1 according to the present disclosure includes a self-inflating elastic squeeze bag 2, a squeeze bag inlet valve housing 5 including a squeeze bag inlet valve arrangement 6, a patient valve housing 7 including a patient valve arrangement 8, and a filter arrangement 11 located inside the squeeze bag 2.

The self-inflating elastic squeeze bag 2 has a support strap 39, a squeeze bag inlet opening 3, a squeeze bag outlet opening 4, a wall 13 defining an inner volume 100, and an inside wall 21.

The squeeze bag inlet valve housing 5 has a circular disc 46 which along its periphery is attached to the squeeze bag inlet opening 3. The central part of the circular disc 46 has the shape of a valve seat with holes 47 which are covered by a thin circular elastic valve flap 48 located on the interior side of the circular disc 46 and which is attached to the valve seat by a centrally located pin 49. The circular elastic valve flap 48 together with the valve seat forms a main inlet one-way valve 52 of the inlet valve arrangement 6. The exterior side of the disc 46 is integral with the squeeze bag inlet valve housing 5 having two parallel side walls 50 with holes 51, these side walls forming valve seats for an ambient air intake valve 53 mounted on the inside of the squeeze bag inlet valve housing 5 and a relief valve 54 mounted on the outside of the squeeze bag inlet valve housing 5, respectively. The ambient air intake valve 53 comprises in addition to the holes 51 a thin circular valve flap 55 which is attached to the valve seat by a pin 56. Similarly, the relief valve 54 comprises another thin circular valve flap 57 which is attached to the valve seat by means of a pin 58. The squeeze bag inlet valve housing 5 is at the end opposite to the disc 46 provided with the oxygen reservoir bag connector port 45.

The squeeze bag inlet valve housing 5 has a peripheral inlet valve housing wall 24 which extends beyond the squeeze bag inlet opening 3 and is provided with a number of ambient air inlet openings 25 for the intake of air from the surroundings into the squeeze bag inlet valve housing 5. An end 30 of the squeeze bag inlet valve housing 5 is also shown.

The patient valve housing 7 further includes a patient connection port 9 for directing air to and from the patient airways and a patient expiration outlet port 10 for outlet of exhaled gas from the patient valve housing 7 to the surroundings. The patient valve arrangement 8 includes a single elastic valve flap 59 closing against a squeeze bag outlet valve seat 60 of the patient valve housing 7 and abutting a patient expiration outlet valve seat 61 when the bag 2 is compressed. The single elastic valve flap 59 is held by a valve pin 62. The patient valve housing 7 is provided with a manometer port 40 with cap.

The filter arrangement 11 has the form of a filter bag 19 having a ring-formed peripheral part 20 extending away from the squeeze bag inlet opening 3 and being arranged adjacent the inside wall 21 of the squeeze bag 2. A peripheral edge 12 of the filter arrangement 11 fits a cross-section of a wall 13 of the squeeze bag 2.

Figure 3:
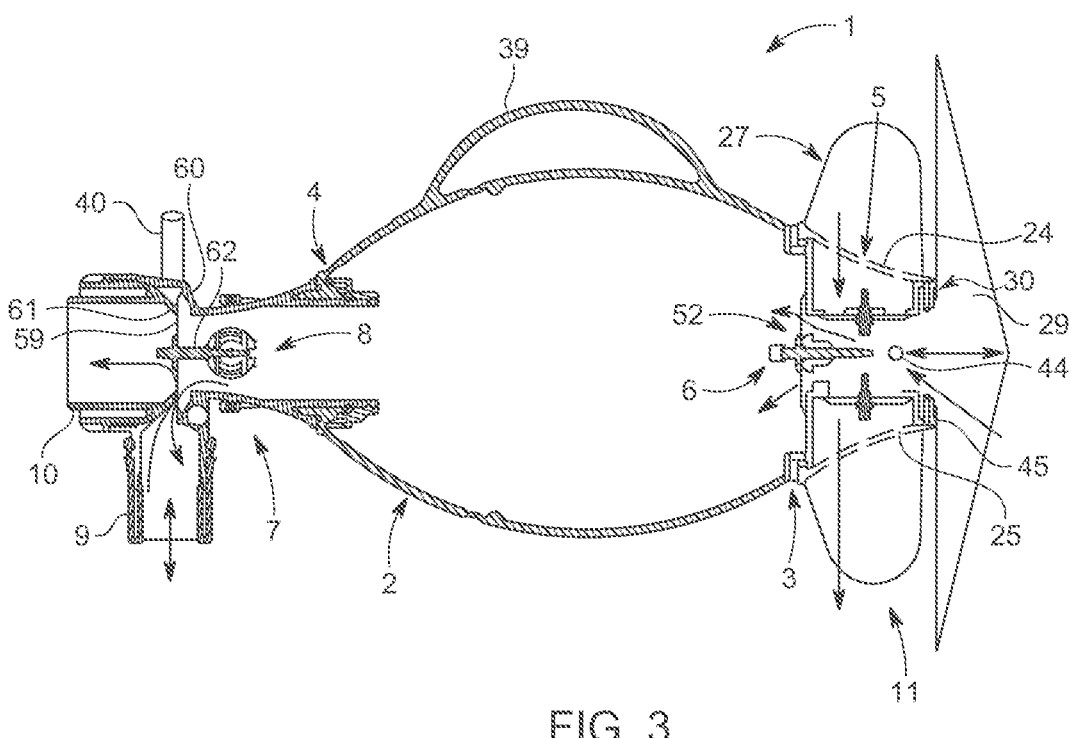

FIG. 3 shows a resuscitator 1 according to the present disclosure that is substantially the same as the resuscitator of FIG. 2, except that the filter arrangement 11 is located outside the squeeze bag 2. The filter arrangement 11 in the present embodiment has the form of a ring-formed filter bag 27 arranged on an outside of the peripheral inlet valve housing wall 24. An oxygen reservoir bag 29 is arranged at the end 30 of the squeeze bag inlet valve housing 5 opposed to the squeeze bag 2.

Figure 4:
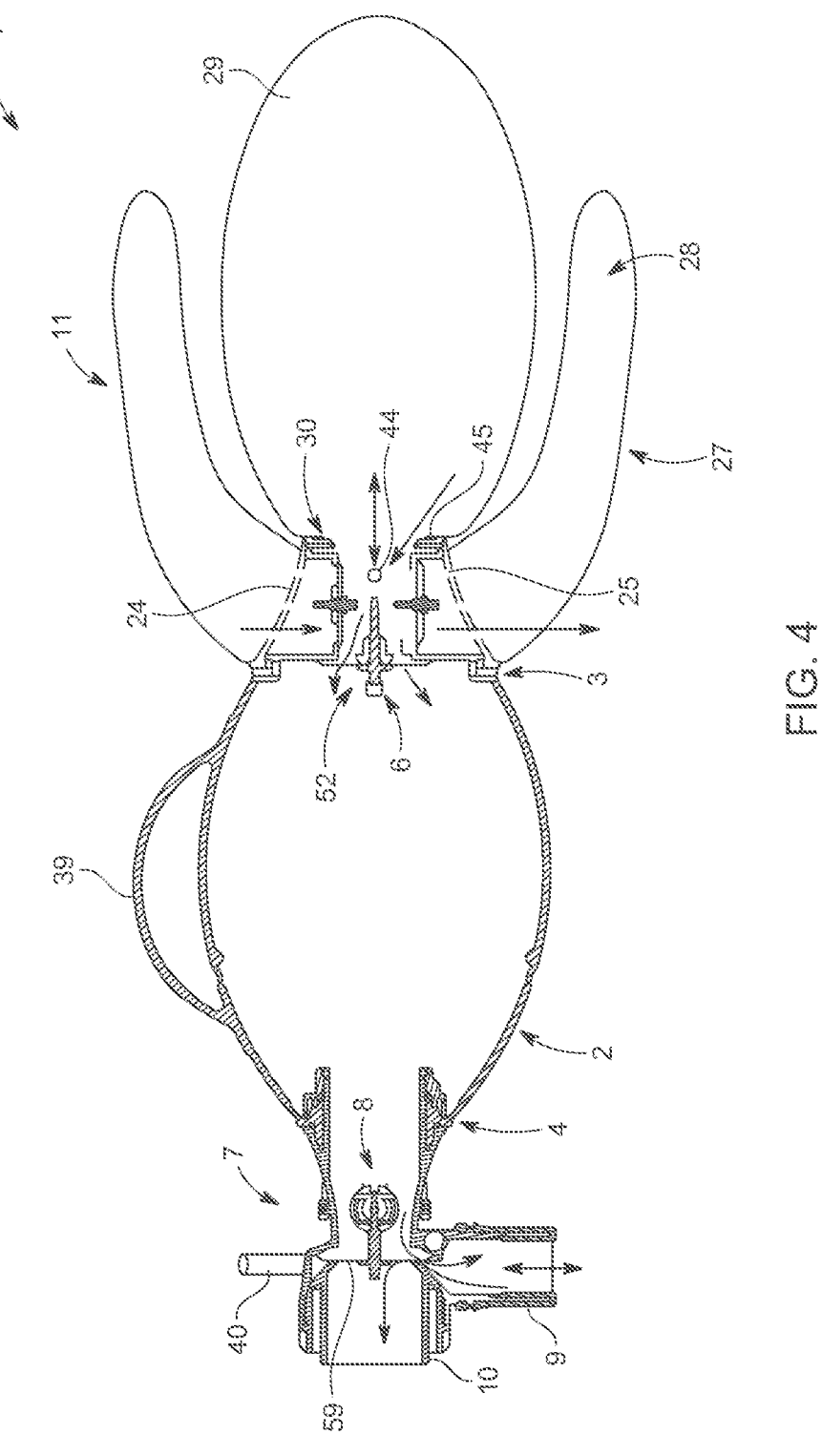

FIG. 4 shows a variation of the resuscitator of FIG. 3, in which the filter bag 27 extends beyond the inlet valve housing 5 in a direction away from the squeeze bag 2. Furthermore, a part 28 of the ring-formed filter bag 27 surrounds the oxygen reservoir bag 29 arranged at the end 30 of the squeeze bag inlet valve housing 5.

In the embodiments illustrated in FIGS. 3 and 4, the ring-formed filter bag 27 may be adapted to be maintained in shape by means of a not shown flexible skeleton. Thereby, similar advantages as those discussed below in connection with the embodiments of FIGS. 12 to 14 may be achieved.

Figure 5:
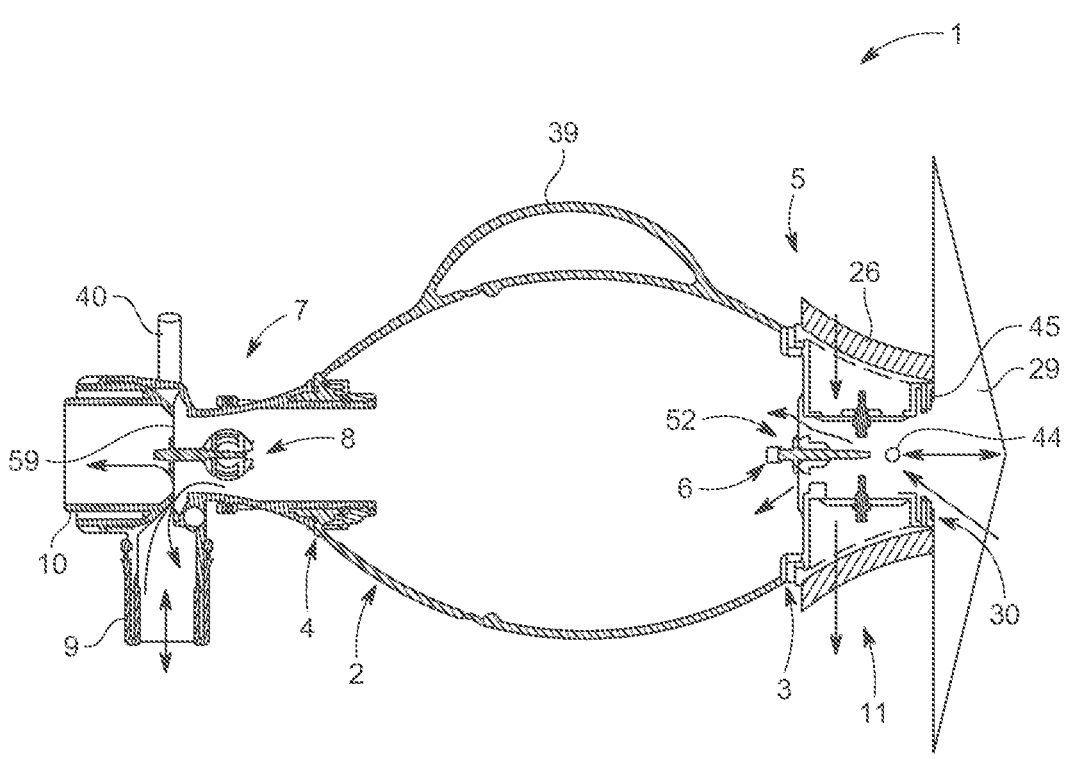

FIG. 5 shows a resuscitator 1 according to the present disclosure that is substantially the same as the resuscitator of FIG. 2, except that the filter arrangement 11 is located outside the squeeze bag 2. The filter arrangement 11 has the form of a filter material 26 covering the outside of the peripheral inlet valve housing wall 24. As shown, the peripheral inlet valve housing wall 24 is curved. The oxygen reservoir bag 29 is also shown. Of course, in these embodiments, filter material 26 could be protected by an external cage or perforated wall, screen, grille, etc.

Figure 6:
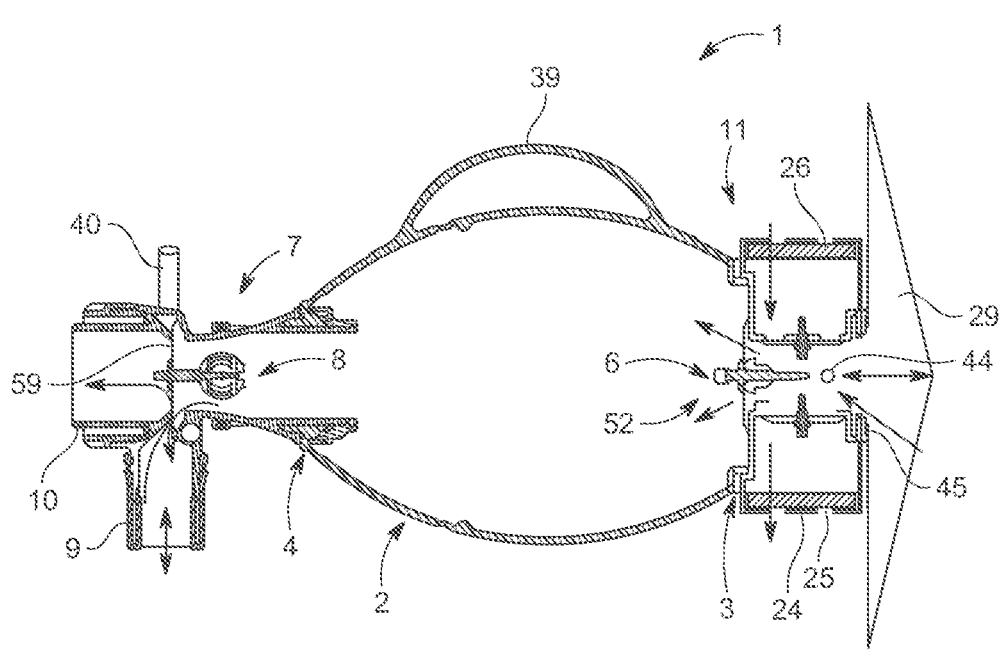
Figure 7:
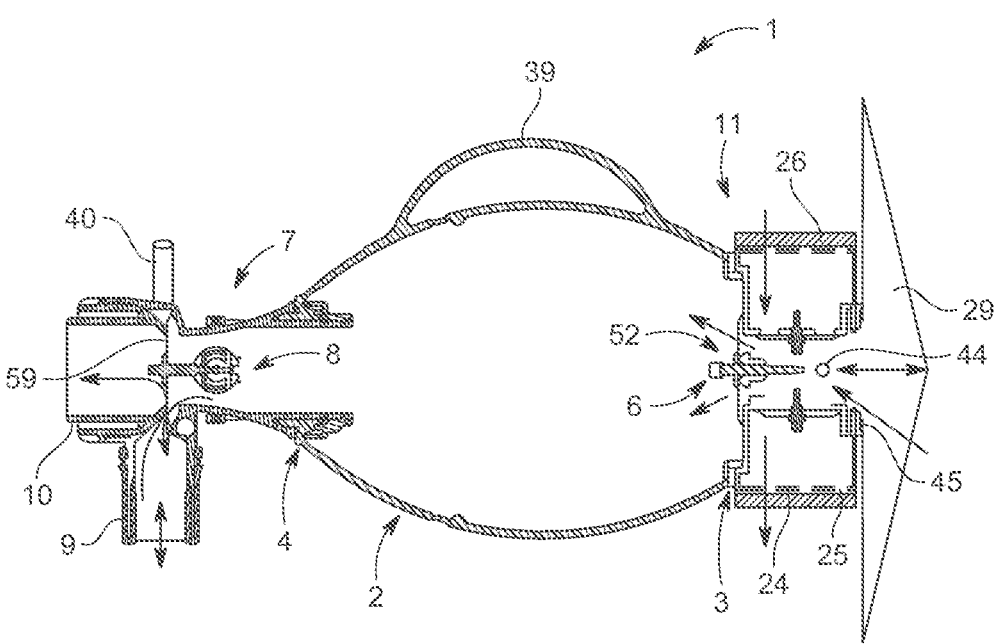

FIGS. 6 and 7 show embodiments of a resuscitator 1 according to the present disclosure that are substantially the same as the resuscitator of FIG. 5, except that the peripheral inlet valve housing wall 24 is positioned outwardly and the filter material 26 covers the inside or the outside, respectively, of the peripheral inlet valve housing wall 24. As shown, the peripheral inlet valve housing wall 24 is straight.

Figure 8:
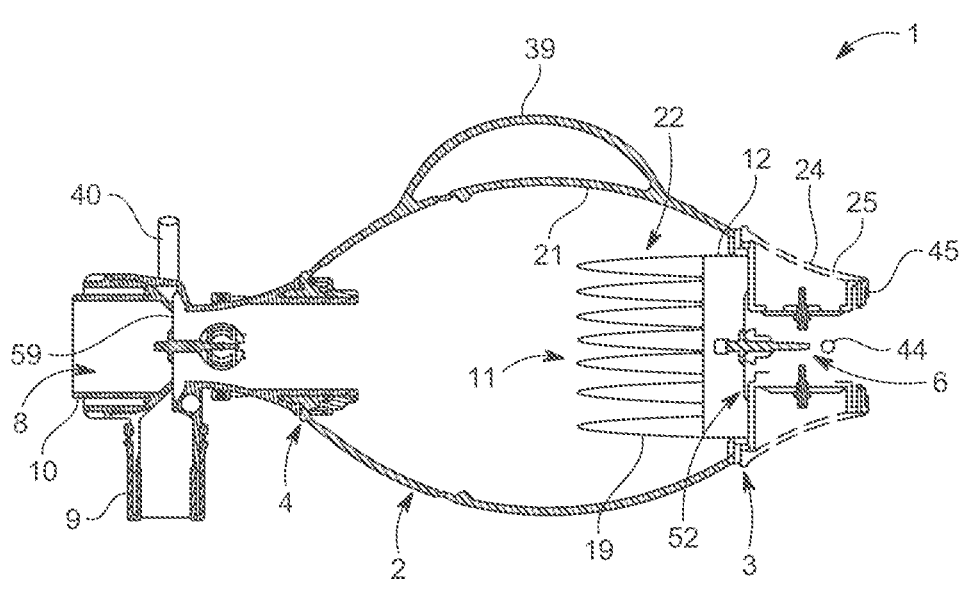

In the embodiment illustrated in FIG. 8, the filter arrangement 11 has the form of a number of filter bags 19 arranged in a ring-form 22 adjacent an inside wall 2 of the squeeze bag 2. Thereby, the influence on the filter arrangement 11 and consequently on the inflation resistance from squeezing the squeeze bag 2 may be minimized, because the number of filter bags 19 arranged in the ring-form 22 may flex towards the inner of the squeeze bag 2 when the squeeze bag is squeezed. Therefore, squeezing the squeeze bag 2 will not result in much air being pressed through the filter bags 19. Furthermore, the number of filter bags 19 arranged in the ring-form 22 may allow packing the resuscitator 1 for transport by pressing opposed ends of the squeeze bag, corresponding to the ends provided with the squeeze bag inlet opening 3 and the squeeze bag outlet opening 4, respectively, into the interior of the squeeze bag 2.

Alternatively, according to the embodiment illustrated in FIG. 8, the filter arrangement 11 may have the form of a number of tapering filter bags 19 arranged evenly or in any suitable distribution over the cross-sectional area of the squeeze bag 2. Advantages of the tapering filter bags 19 may be as described above.

Figure 9:
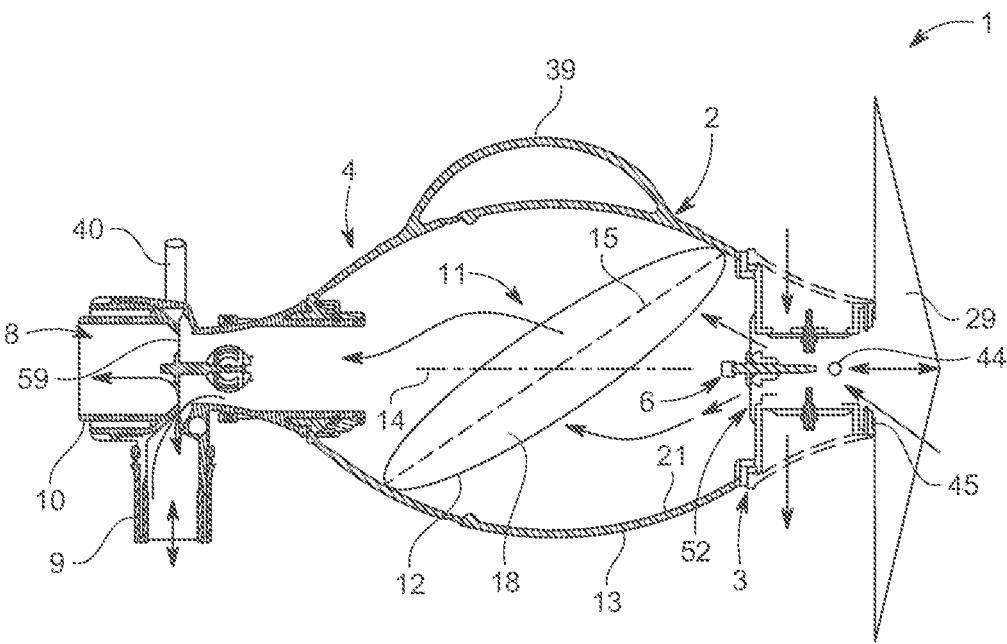

In the embodiment illustrated in FIG. 9, a peripheral edge 12 of the filter arrangement 11 fits a cross-section of a wall 13 of the squeeze bag 2, and the peripheral edge 12 of the filter arrangement 11 is attached to the wall 13 of the squeeze bag 2. In this embodiment, the filter arrangement 11 may be a flat filter 18 or a flat arrangement of a corrugated filter that collapses and expands with the compression and re-expansion of the squeeze bag 2. The filter arrangement 11 may be attached to an inside wall 22 of the squeeze bag 2, e.g. by gluing, hot melt etc. Alternatively or in addition, the filter arrangement 11 could be provided with a flexible rim that is attached and held in position by friction or by being glued, e.g. between protrusions or shoulders, on the inside wall 22 of the squeeze bag 2.

In a further variation of the embodiment illustrated in FIG. 9, the peripheral edge 12 of the filter arrangement 11 has been attached to the wall 13 of the squeeze bag 2 by assembling the squeeze bag 2 from two complementary squeeze bag parts and sandwiching the peripheral edge 12 of the filter arrangement between opposed edges of the complementary squeeze bag parts. After arranging the filter arrangement 11 inside a first squeeze bag part, the two squeeze bag parts of the squeeze bag is assembled, e.g. by gluing and/or hot melt, etc. The filter arrangement 11 may thereby be attached to the inside of the squeeze bag 2 prior to or during assembly of the bag, e.g. by gluing and/or hot melt etc.

As further seen, in the embodiment illustrated in FIG. 9, the squeeze bag 2 is elongated in a longitudinal direction 14 extending from the squeeze bag inlet opening 3 to the squeeze bag outlet opening 4, and the filter arrangement 11 has a longitudinal direction 15 being arranged obliquely to the longitudinal direction 14 of the squeeze bag 2. Thereby, the filter area of the filter arrangement 11 may be maximized. In particular, the filter area of a flat filter 18 in the form of a single sheet filter may be maximized.

Figure 10:
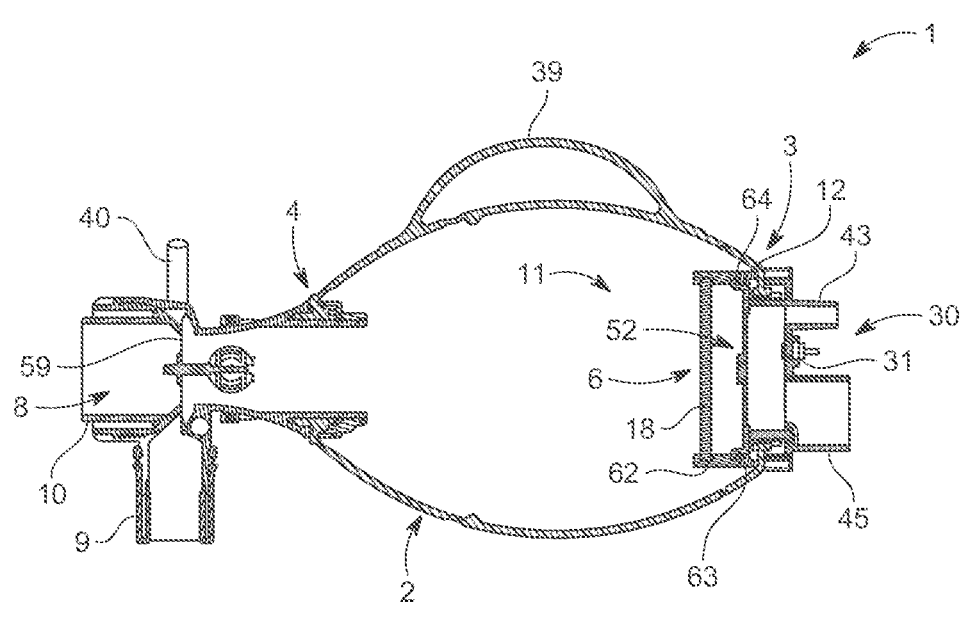
Figure 11:
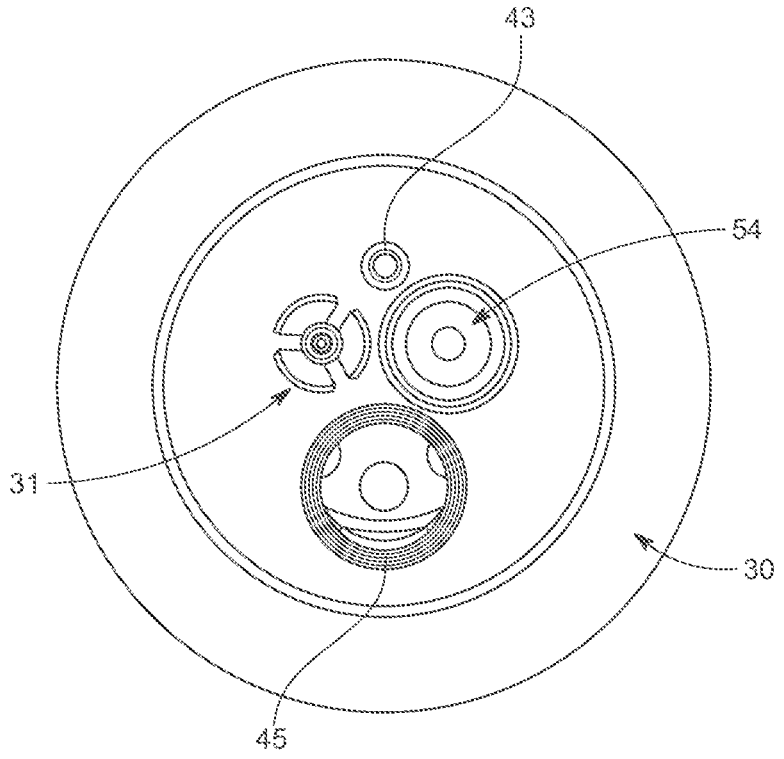
FIG. 11 illustrates an inlet valve housing end wall of the resuscitator of FIG. 10.
Figure 12:
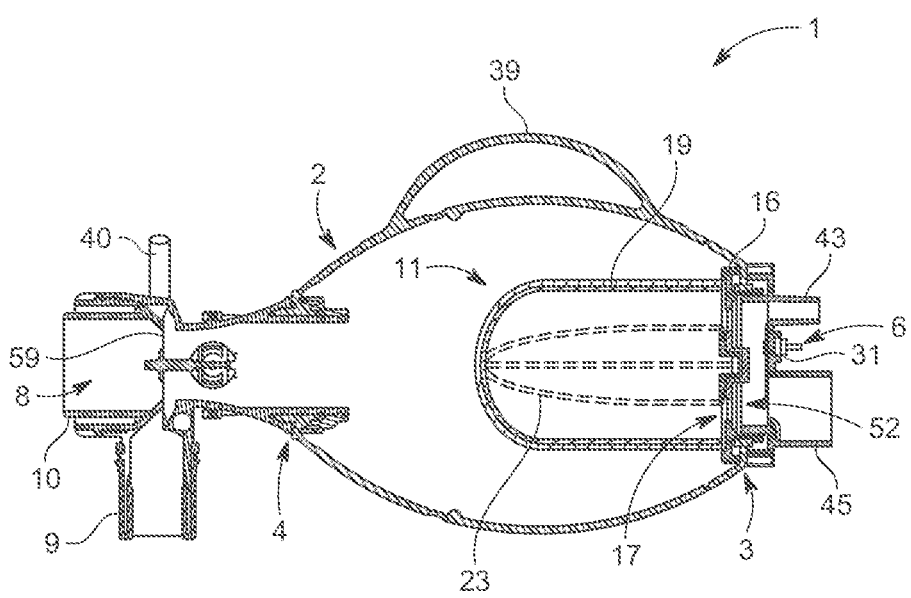
FIG. 12 illustrates, seen in an axial section, yet a different embodiment of a resuscitator with a filter arrangement according to the present disclosure.
Figure 13:
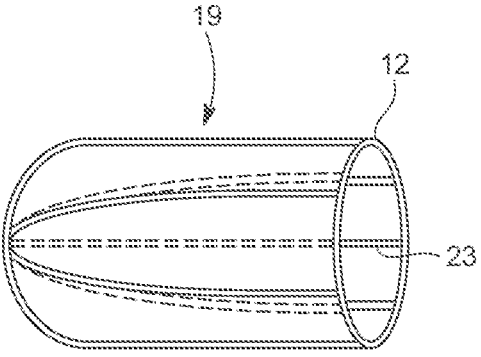
FIG. 13 is a perspective view of the filter arrangement of the resuscitator of FIG. 12.

In the embodiments illustrated in FIGS. 10 to 18, the inlet valve arrangement 6 is arranged in the squeeze bag inlet valve housing 5 as follows. As indicated in FIG. 10, the squeeze bag inlet valve housing 5 has a main inlet one-way valve 52 corresponding largely to the main inlet one-way valve 52 of the embodiment of FIGS. 2 to 9 and 23 to 25, although of slightly different construction. The end 30 of squeeze bag inlet valve housing 5 facing away from the squeeze bag 2 is provided with an ambient air inlet valve 31 corresponding to the ambient air inlet valve 53 of the embodiments of FIGS. 2 to 9 and 23 to 25. As seen in FIG. 11, the end 30 of squeeze bag inlet valve housing 5 is also provided with a relief valve 54 corresponding to that of the embodiment of FIGS. 2 to 9 and 23 to 25.

The skilled person will understand that although different types of the squeeze bag inlet valve housing 5 and inlet valve arrangement 6 have been illustrated in the figures, all different types of filter arrangements 11 described and illustrated in the different figures may be employed irrespectively of the type of squeeze bag inlet valve housing 5 and inlet valve arrangement 6 employed. Nevertheless, some simple modifications of the squeeze bag inlet valve housing 5 and inlet valve arrangement 6 may be necessary in order to fit a different type of filter arrangement 11 that shown in the respective figures. For instance, the filter arrangements 11 illustrated in FIGS. 2, 8, 9, 12, 14 and 23 to 25 may be applied to the squeeze bag inlet valve housing 5 and inlet valve arrangement 6 illustrated in FIG. 10 without any substantial modifications of the squeeze bag inlet valve housing 5 or the inlet valve arrangement 6. The other way around, the filter arrangement 11 illustrated in FIG. 10 may be applied to the squeeze bag inlet valve housing 5 and inlet valve arrangement 6 illustrated in FIGS. 2, 8, 9, 12, 14 and 23 to 25 without any substantial modifications of the squeeze bag inlet valve housing 5 or the inlet valve arrangement 6.

In all illustrated embodiments, as seen for instance in FIG. 3, the patient valve arrangement 8 includes a single elastic valve flap 59 closing against a squeeze bag outlet valve seat 60 of the patient valve housing 7 in its relaxed state when the squeeze bag 2 is not compressed by an operator. In this state, the single valve flap 59 allows the patient to exhale through the patient connection port 9 and the patient expiration outlet port 10, and further prevents inflow of air into the squeeze bag 2 through the squeeze bag outlet opening 4. On the other hand, when the squeeze bag 2 is compressed by an operator or the patient is inhaling spontaneously through the resuscitator, the single elastic valve flap 59 abuts a patient expiration outlet valve seat 61, thereby preventing communication between the patient connection port 9 and the patient expiration outlet port 10, and the single valve flap 59 allows outflow of air from the squeeze bag 2 through the squeeze bag outlet opening 4, into the patient valve housing 7 and further into the patient connection port 9 in order to ventilate the patient. The single elastic valve flap 59 is held by a valve pin 62.

In the embodiments illustrated in FIGS. 2, 8, 9, 10, 12, 14 and 23 to 25, the filter arrangement 11 is located inside the squeeze bag 2. This may have the advantage that the overall dimensions of the resuscitator 1 may be unaffected by the filter arrangement 11, and the resuscitator 1 will be less bulky when the filter arrangement 11 is located inside the squeeze bag 2. Furthermore, it may be an advantage that the effective filtration area may be maximized which may reduce inspiratory resistance.

In the embodiments illustrated in FIGS. 2, 8, 10, 12, 14, 24 and 25, the filter arrangement 11 is attached at the squeeze bag inlet opening 3. Thereby, when the squeeze bag is compressed, the inflation resistance may be influenced very little or not at all, depending on how much or whether the filter arrangement 11 itself is deformed when squeezing the squeeze bag 2. If the filter arrangement 11 itself is not deformed when squeezing the squeeze bag 2, the inflation resistance may not at all be influenced by the filter arrangement 11. It is noted that when placing the filter arrangement 11 at the squeeze bag inlet opening 3, the compressed squeeze bag 2, when let free from its compression by an operator, will by means of its elasticity in practice drag respiration air in through the filter arrangement 11.

Figure 24:
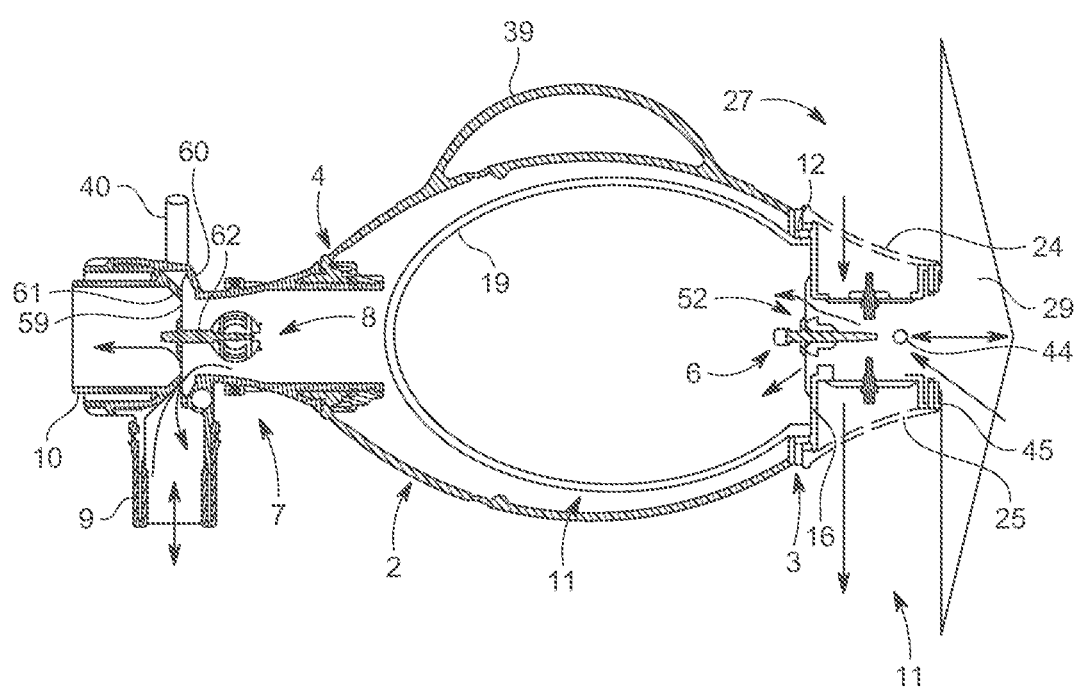

As an example, in the embodiment of FIG. 24, the filter arrangement 11 takes up a relatively large part of the inner volume 100 of the squeeze bag 2 and is therefore substantially deformed when squeezing the squeeze bag 2. On the other hand, in the embodiment of FIG. 25, the filter arrangement 11 takes up a relatively small part of the inner volume of the squeeze bag 2 and is arranged so that it is relatively little deformed when squeezing the squeeze bag 2. Therefore, when the squeeze bag of the embodiment of FIG. 24 is compressed, the inflation resistance may be influenced relatively more than it is the case when the squeeze bag of the embodiment of FIG. 25 is compressed.

Furthermore, in the embodiments illustrated in FIGS. 2, 8, 10, 12, 14, 24 and 25, the filter arrangement 11 is advantageously attached to the squeeze bag inlet valve housing 5. More specifically, the filter arrangement 11 has a peripheral edge 12 attached along a corresponding edge 16 of a filter opening 17 of the squeeze bag inlet valve housing 5.

However, alternatively, in these embodiments, the filter arrangement 11 could be attached directly to the inside wall 22 of the squeeze bag 2.

Apart from the embodiment illustrated in FIG. 9, also in the embodiment illustrated in FIGS. 10 and 23, the filter arrangement 11 has the form of a flat filter 18. According to these embodiments, the filter arrangement 11 does not need to be flexible, because compression of the squeeze bag 2 does not also compress the flat filter 18. In the embodiment of FIG. 10, the filter arrangement 11 may be attached by means of a compression ring 62 having a protrusion 63 mating with a corresponding cut-out 64 at the end of the squeeze bag inlet valve housing 5 arranged inside the squeeze bag 2. Alternatively, the filter arrangement 11 may be attached to the squeeze bag inlet valve housing 5 by means of gluing or by using hot melt.

In the embodiments illustrated in FIGS. 2, 8, 12, 14, 24 and 25, the filter arrangement 11 includes one or more pocket filters and/or filter bags 19.

In particular, in the embodiment illustrated in FIG. 2, the filter arrangement 11 has the form of a filter bag 19 having a ring-formed peripheral part 20 extending away from the squeeze bag inlet opening 3 and being arranged adjacent an inside wall 21 of the squeeze bag 2. Thereby, the influence on the filter arrangement 11 and consequently on the inflation resistance from squeezing the squeeze bag 2 may be minimized, because the ring-formed peripheral part 20 extending away from the squeeze bag inlet opening 3 may flex towards the inner of the squeeze bag 2 when the squeeze bag is squeezed. Therefore, squeezing the squeeze bag 2 will not result in much air being pressed through the filter bag 19. Furthermore, the form of the filter bag 19 having a ring-formed peripheral part 20 extending away from the squeeze bag inlet opening 3 may allow packing the resuscitator for transport by pressing opposed ends of the squeeze bag 2, corresponding to the ends provided with the squeeze bag inlet opening 3 and the squeeze bag outlet opening 4, respectively, into the interior of the squeeze bag 2.

Figure 14:
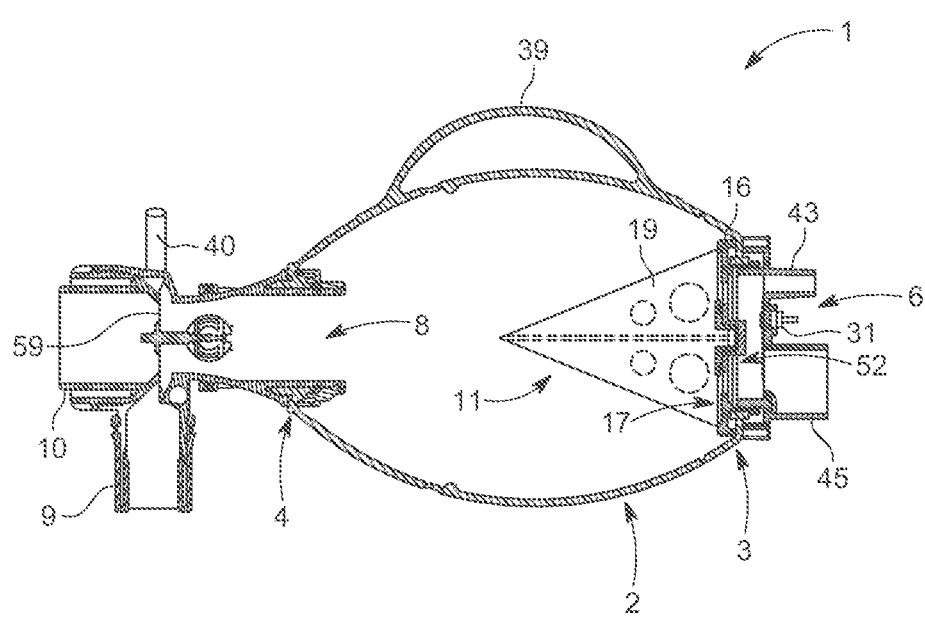
FIG. 14 illustrates, seen in an axial section, yet a different embodiment of a resuscitator with a filter arrangement according to the present disclosure.
Figure 15:
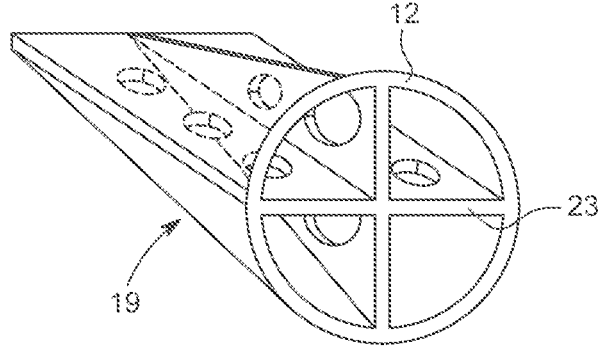
FIG. 15 is a perspective view of the filter arrangement of the resuscitator of FIG. 14.

In particular, in the embodiments illustrated in FIGS. 8, 14 and 25, the filter arrangement 11 has the form of a pocket filter or filter bag 19 being tapered in a direction extending away from the squeeze bag inlet opening 3. Thereby, the influence on the filter arrangement 11 and consequently on the inflation resistance from squeezing the squeeze bag 2 may be minimized, because the volume of air inside the pocket filter or filter bag 19 may be less at a central area of the squeeze bag 2 where the squeeze bag 2 is squeezed.

In particular, in the embodiment illustrated in FIG. 24, the filter arrangement 11 has the form of a relatively large balloon-formed pocket filter or filter bag 19 taking up most of the internal volume of the squeeze bag 2 when the squeeze bag 2 is not compressed by an operator. Thereby, the effective filtration area may be maximized. According to this embodiment, the internal wall of the squeeze bag 2 could be provided with a number of protrusions, such as dot-like knobs or bosses, providing for a certain space between the balloon-formed pocket filter or filter bag 19 and the internal wall of the squeeze bag 2 and thereby avoiding that the filter material contacts the internal wall. Furthermore, it is preferred that the balloon-formed pocket filter or filter bag 19 is prevented from being pressed close against the inlet of the patient valve arrangement 8. This could be done by adapting the size of the balloon-formed pocket filter or filter bag 19, in particular in its lengthwise direction, or by providing the circumference of the inlet of the patient valve arrangement 8 in the squeeze bag 2 with protrusions or indentations.

In particular, in the embodiment illustrated in FIGS. 25 to 27, the filter arrangement 11 has the form of a pocket filter or filter bag 19 being tapered in a direction extending away from the squeeze bag inlet opening 3. As seen, the pocket filter or filter bag 19 is provided with a circular peripheral edge 12 attached along a corresponding edge 16 of a filter opening 17 of the squeeze bag inlet valve housing 5. Alternatively, the filter arrangement 11 could be attached directly to the inside wall 22 of the squeeze bag 2. According to this embodiment, the pocket filter or filter bag 19 is rather flat and slightly V-formed when seen from above in FIG. 25, as illustrated in FIG. 27. On the other hand, when seen in the vertical cross-section of FIG. 25, the pocket filter or filter bag 19 has a rectangular circumference. As seen in FIG. 26, the pocket filter or filter bag 19 has a thin vertically arranged free end part. When the squeeze bag 2 is operated, it is held by the handle 39 and compressed symmetrically about the vertical cross-sectional plane. Thereby, the influence on the filter arrangement 11 and consequently on the inflation resistance from squeezing the squeeze bag 2 may be minimized, because the pocket filter or filter bag 19 is so thin in the compression direction of the squeeze bag 2 that the pocket filter or filter bag 19 is very little compressed.

In the embodiment illustrated in FIG. 8, the filter arrangement 11 has the form of a number of filter bags 19 arranged in a ring-form 22 adjacent an inside wall 2 of the squeeze bag 2. Alternatively, according to the embodiment illustrated in FIG. 8, the filter arrangement 11 may have the form of a number of tapering filter bags 19 arranged evenly or in any suitable distribution over the cross-sectional area of the squeeze bag 2.

As illustrated in the embodiments seen in FIGS. 12 to 15, the one or more pocket filters and/or filter bags 19 is/are adapted to be maintained in shape by means of a flexible skeleton 23. Thereby, it may be ensured that the one or more pocket filters and/or filter bags 19 are maintained in their optimal shape for filtering when the squeeze bag 2 flexes elastically back to its normal form after it has been squeezed. A flexible skeleton 23 may likewise be employed in the pocket filters and/or filter bags 19 of the embodiments of FIGS. 2 and 8.

In the embodiments illustrated in FIGS. 3 to 7 and 16 to 18, the filter arrangement 11 is located outside the squeeze bag 2.

In the embodiments illustrated in FIGS. 2 to 9 and 23 to 25, the squeeze bag inlet valve housing 5 has a peripheral inlet valve housing wall 24 which extends beyond the squeeze bag inlet opening 3 and is provided with a number of ambient air inlet openings 25 for the intake of air from the surroundings into the squeeze bag inlet valve housing 5.

In the embodiments illustrated in FIGS. 6 and 7, the peripheral inlet valve housing wall 24 is cylindrical. In the embodiments illustrated in FIGS. 2 to 5, 8, 9 and 23 to 25, the peripheral inlet valve housing wall 24 is tapering in a direction away from the squeeze bag 2.

In particular, in the embodiments illustrated in FIGS. 3 to 7, the filter arrangement 11 is arranged to filter air flowing through the ambient air inlet openings 25.

In particular, in the embodiment illustrated in FIG. 6, the filter arrangement 11 has the form of a filter material 26 covering an inside of the peripheral inlet valve housing wall 24.

In particular, in the embodiments illustrated in FIGS. 3 to 5 and 7, the filter arrangement 11 has the form of a filter material 26 covering an outside of the peripheral inlet valve housing wall 24. Of course, in these embodiments, filter material 26 could be protected by some sort of external cage or perforated wall, screen, grille, etc.

In particular, in the embodiment illustrated in FIG. 3, the filter arrangement 11 has the form of a ring-formed filter bag 27 arranged on an outside of the peripheral inlet valve housing wall 24.

In particular, in the embodiment illustrated in FIG. 4, the ring-formed filter bag 27 extends beyond the inlet valve housing 5 in a direction away from the squeeze bag 2. Furthermore, as seen, in this embodiment, a part 28 of the ring-formed filter bag 27 surrounds an oxygen reservoir bag 29 arranged at an end 30 of the squeeze bag inlet valve housing 5 opposed to the squeeze bag 2.

In the embodiments illustrated in FIGS. 3 and 4, the ring-formed filter bag 27 may be adapted to be maintained in shape by means of a not shown flexible skeleton. Thereby, similar advantages as those discussed above in connection with the embodiments of FIGS. 12 to 14 may be achieved.

As mentioned above, in the embodiments illustrated in FIGS. 10 to 18, the squeeze bag inlet valve housing 5 has an inlet valve housing end wall 30 facing away from the squeeze bag 2, and the inlet valve housing end wall 30 is provided with an ambient air inlet valve 31.

Figure 16:
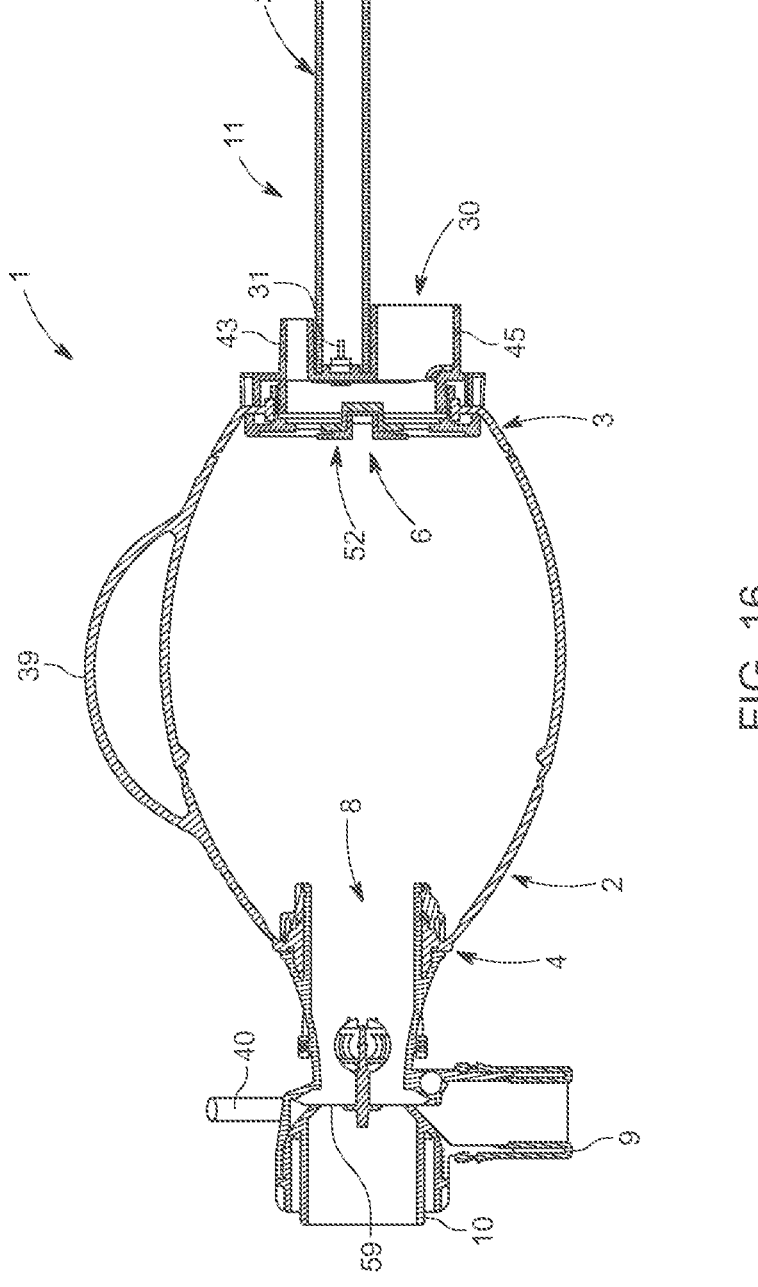
FIGS. 16 and 17 illustrate, seen in an axial section, further different embodiments of a resuscitator with a filter arrangement according to the present disclosure.
Figures 17, 18:
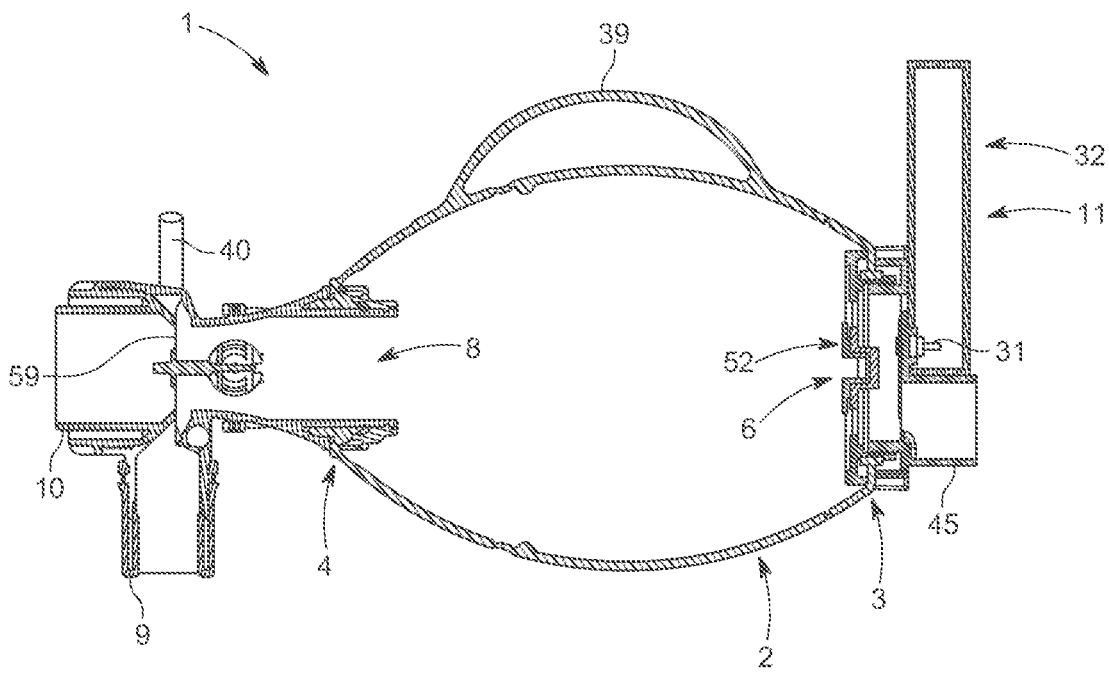
FIG. 18 is a perspective view of the filter arrangement of the resuscitator of FIG. 17.

In the embodiments illustrated in FIGS. 16 to 18, the filter arrangement 11 has the form of a tubular filter 32 extending from the ambient air inlet valve 31. As further seen, the tubular filter 32 extends in a direction away from the squeeze bag 2, which direction may be in a longitudinal direction of the squeeze bag 2, as seen in FIG. 16, or in a transverse direction to the inlet valve housing 5, as illustrated in FIGS. 17 and 18. It is noted that in the embodiment as illustrated in FIG. 17, the oxygen inlet connector 43 is hidden behind the tubular filter 32.

It may be preferred that the filter arrangement 11 includes a filter material having an effective filtration area which is greater than, preferably at least 25 times, more preferred at least 40 times, and even more preferred at least 50 times a minimum cross-sectional flow area of the patient connection port 9. Thereby, even if the filter arrangement 11 is located inside the squeeze bag 2, the inspiratory resistance may be influenced very little. An effective filtration area (EFA) can be defined as the total area of the filter media that is exposed to the flow of liquid or air, that is usable for filtration. This may for instance be designated in square centimetres (cm²).

The filter arrangement 11 may include a filter material based on textiles. The filter arrangement 11 may generally include a bacterial and/or viral filter. Such a filter arrangement 11 may be able to remove up to 99.99% or 99.9999% of bacteria or virus from air.

The filter arrangement 11 may typically include a single layer or usually multiple layers of non-woven textiles made from fibres of polyester, polypropylene, acrylics or polystyrene or mixtures thereof. Alternatively, two, three or more layers (e.g. of different arrangements) of the same fibre or fibre mixture may be used. Each layer may be of different fibres and/or different arrangements. The filter arrangement 11 may typically include at least one (such as two or three) layers of non-woven polypropylene fibres, or a triple layer filter with acrylic/polystyrene nonwoven fibres.

The filter arrangement 11 preferably includes a non-woven polymer fibre layer with a scrim layer on each surface. The filters may be flat or shaped filters with a non-woven fibre layer (e.g. of spun polymer fibers, such as a blend of different synthetic polymer fibers, or one type of fibers, such as spun polypropylene (PP) fibers). The fibres may be treated to have an electrostatic, preferably positive, charged surface. The density of this non-woven filter layer is e.g. between 100 g/m2 and 400 g/m2 (Grams Per Square Meter). The density of the non-woven filter layer is preferably 150-350, more preferred 150-300 even more preferred 150-250 and most preferred 100-200 g/m2. The filter may be provided with scrim layers, such as thin (15 g/m2) layers of hydrophobic textile membrane (of non-woven polymer, e.g. a polypropylene (PP)) on both surfaces of the non-woven layer.

The electrostatic charge on the surface of the fibres attract aerosols or particles that may carry microbes or virus. Most airborne bacteria and virus use aerosols as a transport media. The aerosols are produced when people sneeze or cough. The surface charge of the aerosols results in that the aerosols are attracted to the electrostatically charged filter material, thus providing an improved filter efficiency. An example of suitable commercially available electrostatic filters are e.g. TECHNOSTAT® or TECHNOSTAT PLUS by Hollingsworth & Vose.

As mentioned above, the patient expiration outlet port 10 of a prior art resuscitator as illustrated in FIG. 1 or of a resuscitator according to the present disclosure as illustrated in any of the FIGS. 2 to 18, may be provided with a PEEP valve 33 for the control of the flow and/or pressure at the patient expiration outlet port 10. FIGS. 19 to 22 illustrates a PEEP valve 33 according to the present disclosure, which PEEP valve 33 may be fitted on any of the resuscitators as illustrated in FIGS. 1 to 18, or on any other suitable prior art resuscitator, wherein the PEEP valve 33 has a PEEP valve filter 34. This may reduce and/or eliminate that the operator is exposed to pathogens (bacteria and/or virus) while manually ventilating a contagious patient using the resuscitator.

As seen in FIGS. 19 to 22, the PEEP valve 33 includes a PEEP valve housing 35 having a peripheral PEEP valve housing wall 36, wherein the peripheral PEEP valve housing wall 36 is provided with a number of patient expiration outlet openings 37 for outlet of exhaled gas from the PEEP valve housing 35 to the surroundings, and wherein the PEEP valve filter 34 is arranged to filter air flowing through the patient expiration outlet openings 37.

Furthermore, the PEEP valve 33 includes a rotatable handle 65 threaded onto the PEEP valve housing 35 in order to adjust the valve opening of a valve element 66 in relation to a valve seat 67. The rotatable handle 65 is acting on the valve element 66 by means of a compression spring 68 and the valve element 66 is guided by means of a spindle 69. Furthermore, a tubular element 70 may be arranged between the compression spring 68 and the valve element 66 as seen in FIG. 21.

In the embodiment of FIGS. 21 and 22, the peripheral PEEP valve housing wall 36 is cylindrical.

Figure 19:
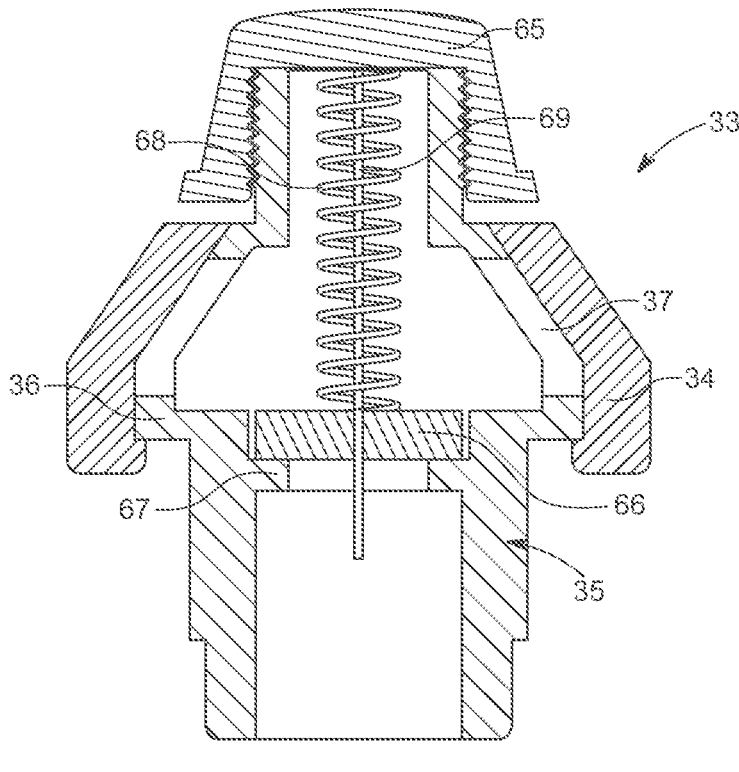
FIG. 19 is an axial section of an embodiment of a PEEP valve with a PEEP valve filter, for use with a resuscitator.
Figure 20:
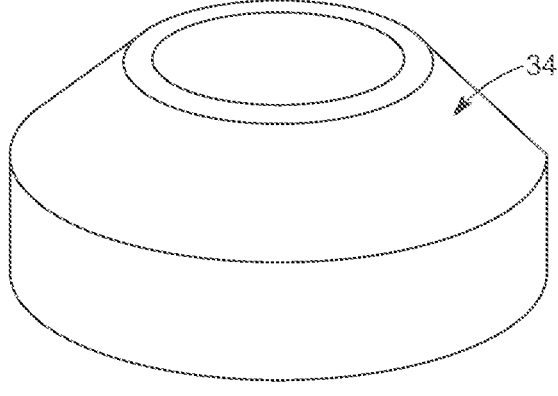
FIG. 20 is a perspective view of the PEEP valve filter of the PEEP valve of FIG. 19.

In the embodiment of FIGS. 19 and 20, the peripheral PEEP valve housing wall 36 is tapering in a direction away from the squeeze bag 2.

As further seen, the PEEP valve filter 34 is covering an outside of the peripheral PEEP valve housing wall 36.

The PEEP valve filter 34 may be integrated in the PEEP valve 33, or the PEEP valve filter 34 may be adapted to click on the PEEP valve 33.

As it is understood, a PEEP valve is a spring loaded valve that a patient may exhale against. "PEEP" is an abbreviation for positive end-expiratory pressure according to a method of ventilation in which airway pressure is maintained above atmospheric pressure at the end of exhalation by means of a mechanical impedance, usually a valve.

LIST OF REFERENCE NUMBERS 1 resuscitator
2 squeeze bag
3 squeeze bag inlet opening
4 squeeze bag outlet opening
5 squeeze bag inlet valve housing
6 squeeze bag inlet valve arrangement
7 patient valve housing
8 patient valve arrangement
9 patient connection port
10 patient expiration outlet port
11 filter arrangement
12 peripheral edge of filter arrangement
13 wall of squeeze bag
14 longitudinal direction of squeeze bag
15 longitudinal direction of filter arrangement
16 edge of filter opening of squeeze bag inlet valve housing
17 filter opening
18 flat filter
19 pocket filter and/or filter bag
20 ring-formed peripheral part of filter bag
21 inside wall of squeeze bag
22 ring-form of filter bags
23 flexible skeleton of pocket filter and/or filter bag
24 peripheral inlet valve housing wall
25 ambient air inlet opening
26 filter material
27 ring-formed filter bag
28 part of ring-formed filter bag
29 oxygen reservoir bag
30 end of inlet valve housing
31 ambient air inlet valve
32 tubular filter
33 PEEP valve
34 PEEP valve filter
35 PEEP valve housing
36 PEEP valve housing wall
37 patient expiration outlet opening
38 face mask
39 support strap
40 manometer port
41 M-port
42 pressure limiting valve
43 oxygen inlet connector
44 oxygen inlet port
45 oxygen reservoir bag connector port
46 circular disc
47 holes of valve seat
48 elastic valve flap of main inlet one-way valve
49 centrally located pin of valve seat

50 side wall of squeeze bag inlet valve housing
52 main inlet one-way valve
53 ambient air intake valve
54 relief valve
55 circular valve flap of ambient air intake valve
56 pin of valve seat
57 circular valve flap of relief valve
58 pin of valve seat
59 single elastic valve flap of patient valve housing
60 squeeze bag outlet valve seat
61 patient expiration outlet valve seat
62 compression ring
63 protrusion of compression ring
64 cut-out at squeeze bag inlet valve housing
65 rotatable handle of PEEP valve
66 valve element
67 valve seat
68 compression spring
69 spindle
70 tubular element

The invention claimed is:

1. A resuscitator including:
an inlet valve housing including an inlet valve arrangement;
a patient valve housing including a patient valve arrangement, a patient connection port and a patient expiration outlet port;
a squeeze bag that is self-inflating and comprises a squeeze bag inlet opening, a squeeze bag outlet opening, and a wall extending between the squeeze bag inlet opening and the squeeze bag outlet opening, the squeeze bag inlet opening connected to the inlet valve housing, the squeeze bag outlet opening connected to the patient valve housing, and the wall defining an inner volume of the squeeze bag; and
a filter arrangement located in the inner volume of the squeeze bag.

2. The resuscitator of claim 1, wherein the filter arrangement comprises a filter bag including a ring-formed peripheral part.

3. The resuscitator of claim 2, wherein the ring-formed peripheral part of the filter bag is attached to the inlet valve housing and extends downstream from the squeeze bag inlet opening.

4. The resuscitator of claim 2, wherein the filter arrangement comprises a number of filter bags in addition to the filter bag.

5. The resuscitator of claim 4, wherein the number of filter bags are tapering filter bags.

6. The resuscitator of claim 4, wherein the squeeze bag has an unsqueezed form, wherein the filter arrangement further comprises a flexible skeleton configured to restore a shape of at least one of the number of filter bags when the squeeze bag flexes back to the unsqueezed form.

7. The resuscitator of claim 2, wherein the filter bag takes up more than half of the inner volume of the squeeze bag.

8. The resuscitator of claim 2, wherein a peripheral edge of the filter arrangement is attached to the wall of the squeeze bag.

9. The resuscitator of claim 8, wherein the peripheral edge of the filter arrangement fits a cross-section of the squeeze bag.

10. The resuscitator of claim 9, wherein the squeeze bag is elongated in a longitudinal direction extending from the squeeze bag inlet opening to the squeeze bag outlet opening, and wherein the filter arrangement is arranged obliquely to the longitudinal direction of the squeeze bag.

11. The resuscitator of claim 10, wherein the squeeze bag comprises two complementary squeeze bag parts, and wherein the peripheral edge of the filter arrangement is positioned between opposed edges of the complementary squeeze bag parts.

12. The resuscitator of claim 1, wherein the filter arrangement comprises a flat filter.

13. The resuscitator of claim 12, wherein the flat filter comprises a flat surface and is attached to the patient valve housing or the inlet valve housing.

14. The resuscitator of claim 13, wherein the flat surface is orthogonal to a longitudinal extent of the squeeze bag.

15. The resuscitator of claim 1, wherein the patient expiration outlet port is provided with a positive end-expiratory pressure (PEEP) valve, and wherein the PEEP valve has a PEEP valve filter.

16. A resuscitator including:
an inlet valve housing including an inlet valve arrangement;
a patient valve housing including a patient valve arrangement, a patient connection port and a patient expiration outlet port;
a squeeze bag that is self-inflating and comprises a squeeze bag inlet opening, a squeeze bag outlet opening, and a wall extending between the squeeze bag inlet opening and the squeeze bag outlet opening, the squeeze bag inlet opening connected to the inlet valve housing, the squeeze bag outlet opening connected to the patient valve housing, and the wall defining an inner volume of the squeeze bag; and
a filter arrangement located in the inner volume of the squeeze bag,
wherein the filter arrangement includes a first scrim layer, a second scrim layer, and a non-woven polymer fibre layer between the first scrim layer and the second scrim layer.

17. The resuscitator of claim 16, wherein a density of the non-woven polymer fibre layer is between 150 $g/m^2$ and 300 $g/m^2$.

18. The resuscitator of claim 16, wherein a density of the non-woven polymer fibre layer is between 100 $g/m^2$ and 200 $g/m^2$.

19. A resuscitator including:
an inlet valve housing including an inlet valve arrangement;
a patient valve housing including a patient valve arrangement, a patient connection port and a patient expiration outlet port;
a squeeze bag that is self-inflating and comprises a squeeze bag inlet opening, a squeeze bag outlet opening, and a wall extending between the squeeze bag inlet opening and the squeeze bag outlet opening, the squeeze bag inlet opening connected to the inlet valve housing, the squeeze bag outlet opening connected to the patient valve housing, and the wall defining an inner volume of the squeeze bag; and
a filter arrangement located in the inner volume of the squeeze bag,
wherein the patient connection port comprises a minimum cross-sectional flow area, and wherein the filter arrangement comprises a filter material having a filtration area which is at least 25 times larger than the minimum cross-sectional flow area of the patient connection port.

20. A resuscitator according to claim 19, wherein the filtration area is at least 40 times larger than the minimum cross-sectional flow area of the patient connection port.

\* \* \* \* \*